United States Patent [19]
Lepinoy

[11] Patent Number: 5,240,135
[45] Date of Patent: Aug. 31, 1993

[54] RIGID WRAPAROUND SHELL DEFINING A SEALED INNER SPACE

[75] Inventor: Dominique Lepinoy, Dijon, France
[73] Assignee: Lepinoy Industrie, Dijon, France
[21] Appl. No.: 860,513
[22] PCT Filed: Oct. 16, 1990
[86] PCT No.: PCT/FR90/00743
§ 371 Date: Jun. 16, 1992
§ 102(e) Date: Jun. 16, 1992
[87] PCT Pub. No.: WO91/05720
PCT Pub. Date: May 2, 1991

[30] Foreign Application Priority Data
Oct. 16, 1989 [FR] France .................. 89 13479

[51] Int. Cl.$^5$ .................................. B65D 45/00
[52] U.S. Cl. .................... 220/429; 206/522; 428/542.8
[58] Field of Search ........ 220/429; 428/542.8; 206/522, 523, 584

[56] References Cited

U.S. PATENT DOCUMENTS

| | | | |
|---|---|---|---|
| 3,138,248 | 6/1964 | Abbott | 206/522 |
| 3,378,864 | 4/1968 | Cornes | 206/522 |
| 3,667,625 | 6/1972 | Lucas | 206/522 |
| 3,745,998 | 7/1973 | Rose . | |
| 4,402,355 | 9/1983 | Wymore et al. | 206/522 |
| 4,493,877 | 1/1985 | Burnett . | |
| 4,591,519 | 5/1986 | Liebel | 206/522 |
| 4,739,884 | 4/1988 | Duplessy | 206/522 |

FOREIGN PATENT DOCUMENTS

| | | |
|---|---|---|
| 1270443 | 10/1960 | France . |
| 2299874 | 2/1975 | France . |
| 2377931 | 1/1977 | France . |
| 1095311 | 6/1964 | United Kingdom . |

Primary Examiner—Joseph Man-Fu Moy
Attorney, Agent, or Firm—Bacon & Thomas

[57] ABSTRACT

A rigid wraparound shell defining an inner space containing at least one sealed chamber is provided. The rigid wraparound shell (1) is comprised of flexible sealing walls (2,3) which together define a sealed enclosure (5) having a lower pressure that the ambient pressure, and of a filler material (7) which completely fills the low-pressure sealed enclosure (5). The filler material (7) is rigid when it is inside the low-pressure sealed enclosure (5) and can be flexible when subjected to ambient pressure. This shell structure is particularly useful in making floating and/or sliding devices such as floats, hulls for boats, windsurfing boards sledges, skis, tanks, devices for holding and/or supporting the human body in a natural position or in a predetermined position, such as anti-bedsore mattresses or cushions and surgical mattresses, and devices for holding and/or supporting at least one object in a cavity such as a piece of luggage, container, a vehicle boot or the like.

54 Claims, 5 Drawing Sheets

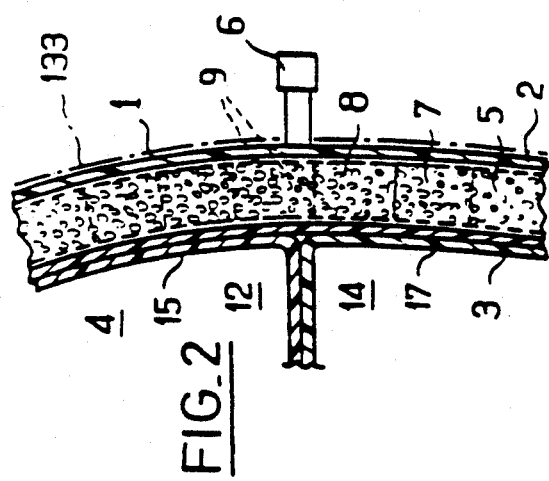
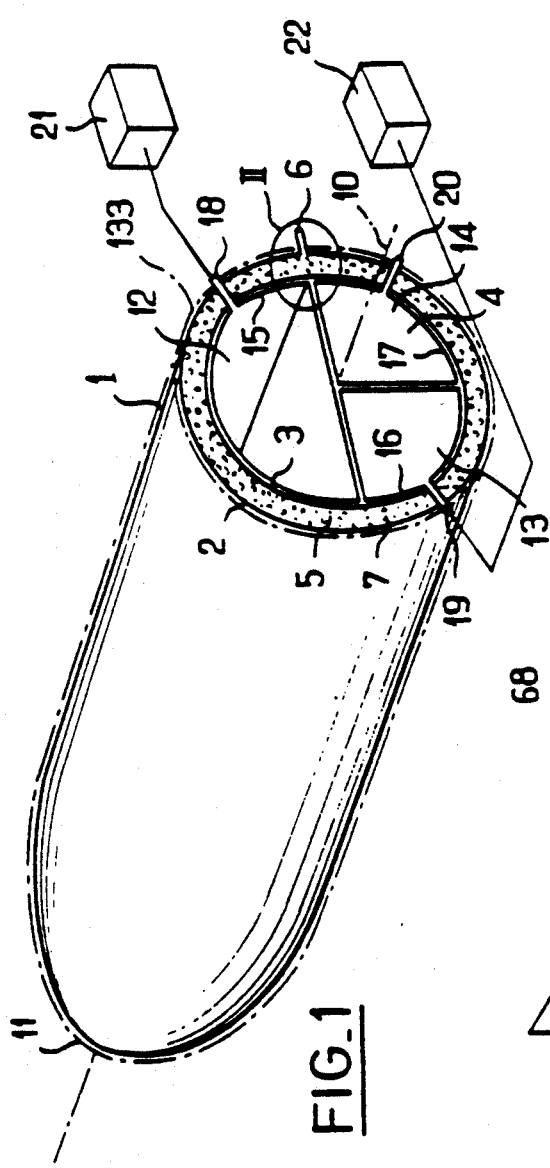
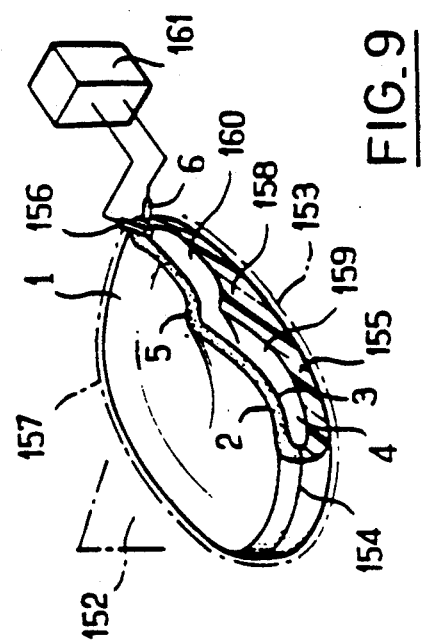
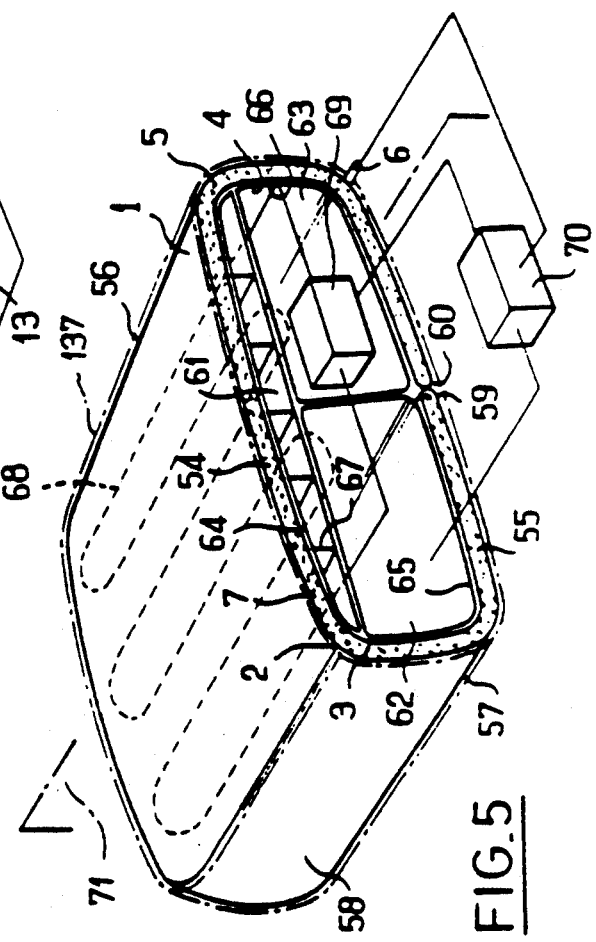

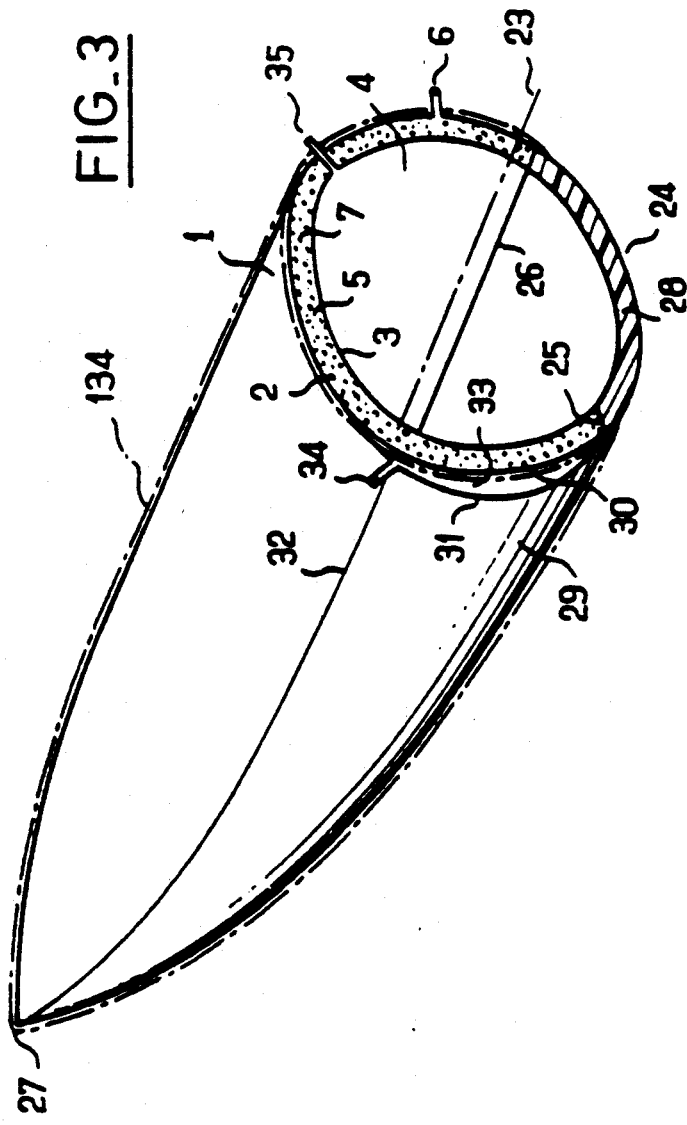
FIG_3
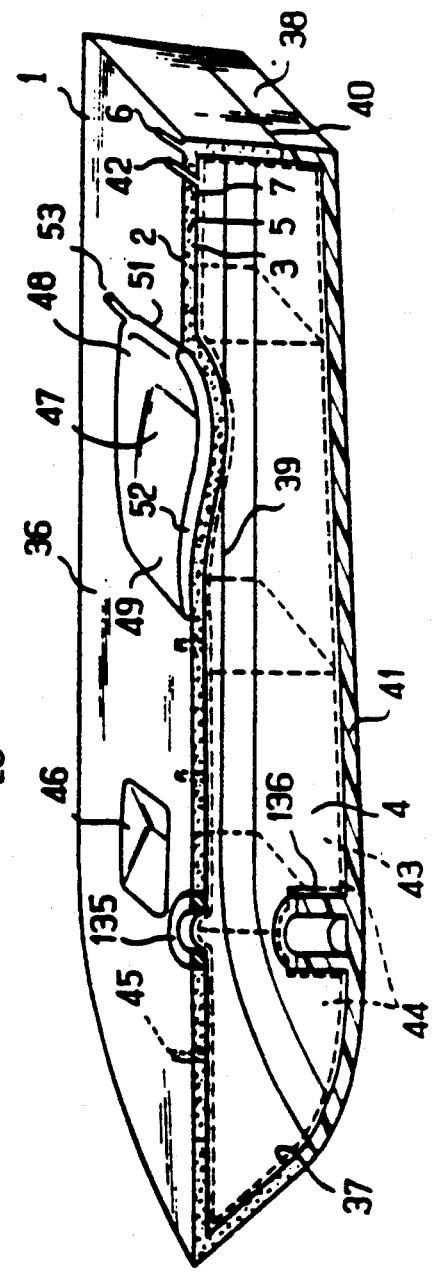
FIG_4

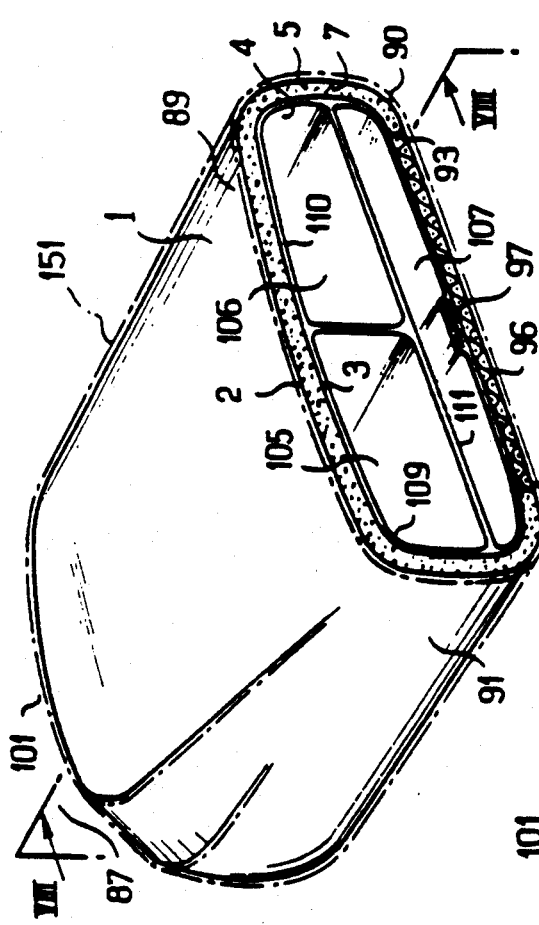
FIG_7
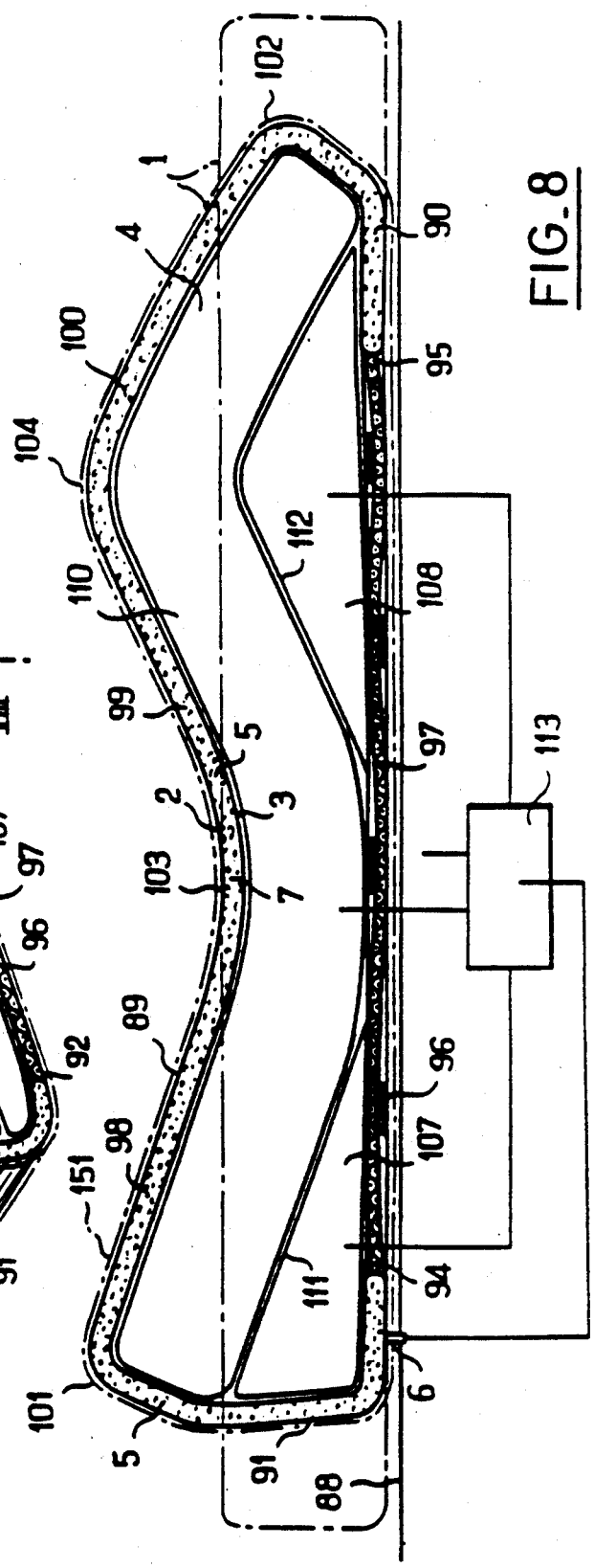
FIG_8

RIGID WRAPAROUND SHELL DEFINING A SEALED INNER SPACE

BACKGROUND OF THE INVENTION

The present invention relates to a device of the type comprising a rigid surrounding shell, delimiting an internal volume, and at least one fluid tight chamber occupying the internal volume.

Devices of this type are numerous and can come from various technical fields.

One can cite for example certain reservoirs, of which the internal fluid tight chamber is intended to receive a fluid which one desires to store in order to be able later to empty this fluid, or again certain floating or sliding devices such as floats particularly of boats, hulls of boats, sail boards, toboggans or skis of which the internal fluid tight chamber can contain a gas or a filling material having a relative density generally less than 1, such as for example a cellular material.

Traditionally, the rigid shell of such devices has been made in metal or thermoplastic or thermosetting material and possibly, particularly in the case of floating devices, in wood so that it has a high weight. Further, as a result of the rigidity of the shell, the device which is provided has a constant shape and volume, causing its handling and storing to be difficult when it is not in use.

To remedy these inconveniences, it has been proposed to replace the rigid shell of certain of these known devices, and in particular of floats and reservoirs, by a flexible membrane surrounding the internal fluid tight chamber of which only filling with fluid at relatively high over-pressure, that is to say at high over-pressure with respect to the pressure present outside this fluid tight chamber, gives the shell a defined shape and its maximum volume, by inflation.

This technique can certainly permit an alleviation, in the case of certain devices as for example the floats of boats, but the necessity of putting the internal fluid tight chamber under high over-pressure renders the putting into service of the device particularly long and laborious, unless one has at one's disposal a compressor itself heavy and voluminous and further requiring a source of energy.

SUMMARY OF THE INVENTION

The object of the present invention is to remedy these inconveniences, by proposing a new method of producing a device of the type discussed above. A further object of the present invention is to increase the possibilities of application of this type of device, particularly in providing embodiments specially adapted to the holding and/or support of the human body in a natural posture or in a predetermined held posture, for example of the anti-bed sore mattress or cushion or surgical mattress type, or again to the holding and/or support of an object in a space having an internal contour, such as a piece of baggage, a container or a luggage compartment of a car.

For this, the device according to the invention, of the type having a rigid surrounding shell, delimiting an internal volume, and at least one internal fluid tight chamber occupying the internal volume, is characterized in that the rigid surrounding shell is constituted by flexible, fluid tight walls delimiting between themselves a fluid tight enclosure held at a pressure below ambient pressure, and of a filling material completely filling the fluid tight enclosure held below ambient pressure, the filling material being of a type having a rigid state in the fluid tight enclosure held below ambient pressure and able to have a flexible state when it is at ambient pressure.

The filling material can be for example a granular material secured throughout an array permeable to gas or liquid but impermeable to this granular material, in order to ensure a predetermined distribution before the establishment of the pressure below ambient in the fluid tight enclosure, as taught by WO 87/06209 which cites by way of non-limitative examples of granular material rushed cork, sawdust, micro-balls of the type sold under the trade mark "Vermiculite" and balls of expanded polystyrene, and by way of example of production means of an array permeable to gas and liquid but impermeable to the granular material a partitioning preferably independent of the walls of the enclosure. Such granular materials and such a method of constitution of an array for securing this can also be used for the production of the present invention, it being intended that other types of filling materials able to have a rigid state when they are enclosed in a fluid tight enclosure delimited by flexible walls and held at a pressure below ambient, and a flexible state when they are submitted to ambient pressure will be able to be used without departing from the scope of the invention, particularly as a function of projected use for the device according to the invention, which can imply certain choices as a function of the degree of rigidity desired for the shell.

A man skilled in the art will easily understand that light filling materials will be able to be used whilst giving to the shell, as a result of the evacuation of the fluid tight enclosure in which they are present, a quitable rigidity for applications to the production of floating and/or sliding devices chosen within a group comprising floats, hulls of boats, sail boards, toboggans, skis, of which a certain rigidity constitutes a safety factor for the user, and, often, an imperative condition for the function, or to the production of reservoirs, such as for fluids susceptible to shocks, or again to the production of devices for holding and/or support of the human body in a natural posture or in a predetermined held posture, chosen within a group comprising anti-bed sore mattresses or cushions and surgical mattresses, or of devices for holding and/or support of at least one object in a space such as a piece of baggage, a container, or the luggage compartment of a car or the like. In these applications, to the possibility of obtaining a rigid shell is added the possibility of forming this rigid shell as a function of the requirements, as a result of the possibility of preliminarily placing the fluid tight chamber at ambient pressure so that the filling material has flexibility permitting shaping of the shell. This possibility can also be used for reducing the volume of the device according to the invention when it is not being used, as can be done with a pneumatic dinghy or a pneumatic mattress, of which the subsequent inflation, necessarily at high over-pressure with respect to ambient pressure, constitutes however a long and laborious operation whilst the return of a device according to the invention to its original shape can be carried out by filling of the fluid tight internal chamber with a fluid material such as a gas or a gaseous mixture at a low over-pressure with respect to ambient pressure, for giving the shell its original shape, then evacuating the fluid tight enclosure, inside the shell, for rigidifying this latter, which involves less work.

Naturally as a function of the envisaged applications, a device according to the invention can have numerous ancillary dispositions, in combination or alone.

Particularly, particular embodiments of a device according to the invention are characterized as discussed below.

The device comprises an access valve to the interior of the fluid tight enclosure held below ambient pressure, which permits on the one hand the re-establishment of this depression in the case where it comes to accidentally disappear, with the result of an undesirable flexibility of the rigid shell, and on the other hand operation at will on this depression for causing it to disappear at will permitting or causing the introduction of a gas or a mixture of gases, such as air, at ambient pressure or of a liquid at ambient pressure into the fluid tight enclosure, in order to permit a remodelling of the rigid shell, then re-establishment of this depression, by forced extraction of this gas, or gaseous mixture, or liquid, for once more rigidifying the shell.

The fluid tight internal chamber contains a fluid material chosen within the group comprising gases, gels, liquids, particulate materials, generally at a pressure substantially identical to the ambient pressure although preferably slightly greater than this, since it is not necessary to obtain in the internal enclosure a significant over-pressure insofar as the retention of the shape of the shell is advantageously connected to the rigidity of this latter more than to the pressure established in the fluid tight internal chamber. However, in certain applications, the fluid material can also be placed at a pressure substantially above ambient pressure. Thus, in an application to the production of a reservoir for storing gas or a gaseous mixture, the gas or gaseous mixture contained in the fluid tight internal chamber can be at a greater pressure than ambient pressure, the rigid shell having a sufficient rigidity to resist the expansion of the fluid tight internal chamber even in such a case. Also, in an application to production of a floating or sliding device, the filling of the fluid tight internal chamber with a fluid material at over-pressure with respect to ambient pressure can contribute to the rigidity of the device in complementing the effect of rigidification of the shell. In comparison with known devices, such as reservoirs or floats, of which the fluid tight internal chamber is delimited by a flexible membrane, the replacement of this latter by a rigidified shell evacuated in accordance with the present invention permits for the same value of the over-pressure existing in the fluid tight internal chamber, an increase of the length of life of the devices in reducing the stresses resulting from the over-pressure in the materials constituting it and in the assembly means for these materials, that is to say the risks of tearing, of rupture or of bursting, or permits, for an equivalent length of life, an increase in the over-pressure.

The device comprises means for causing the fluid material to circulate or, in a more general manner, an access valve to the interior of the fluid tight internal chamber.

The device may comprise several fluid tight internal chambers occupying the internal volume, it being understood that it is each of the chambers can have the characteristics enumerated above as regards the fluid tight internal chamber. Thus, in an application to a reservoir, it is possible to provide the fluid tight internal chamber in two sections at least, and further to provide means for, alternatively, introducing a first fluid to be stored into a first of the sections whilst emptying a second of the sections and introducing a second control fluid into the second section driving the fluid to be stored from the first section, which permits the operation in a particular easy manner of the filling and the emptying of the reservoir. In an application to the holding and/or support of the human body, for example in the form of an anti-bed sore mattress or cushion or of a surgical mattress, an application in which the rigid shell preferably has an upper zone of a generally flat shape, a lower zone of generally flat shape, and a peripheral zone in the form of a skirt mutually connecting the upper and lower zones respectively of generally flat shape, one can provide that at least certain of the chambers have the form of mutually juxtaposed studs under the upper zone and/or again that at least certain of the chambers have the form of tubes of the same predetermined longitudinal direction, mutually juxtaposed transversely to the direction, under the upper zone, that others of the chambers have the form of tubes of the same transverse direction, the tubes of the same predetermined longitudinal direction and the tubes of the same transverse direction being mutually superimposed under the upper zone, and to provide further means for causing in a controlled manner a succession of stages consisting of placing the fluid tight enclosure at ambient pressure, inflating or deflating in a predetermined manner certain, determined, of the chambers, re-placing the fluid tight enclosure at a pressure lower than ambient pressure. Preferably, the fluid tight walls delimiting the fluid tight enclosure are comparatively inextensible in the peripheral zone in which they have a restraining role, and comparatively elastically extensible in the upper zone in which they are thus better molded to the user when the fluid tight enclosure is at ambient pressure.

In the case of an anti-bed sore mattress or cushion, it is thus possible to vary the method of distribution of the weight of the body on the upper zone of the rigid shell, acting either manually as required, or in an automatic manner controlled by an automatic controller coupled for example to pressure detectors distributed on the upper zone of the rigid shell and/or to a timer. The use of such an automatic controller, of which the design will come from the normal abilities of the man skilled in the art, permits ensuring a rigorous management of the positioning of the human body on the bed or an armchair in a manner to spread out statistically during the day the abutment zones of the body on the mattress or cushion, and the pressures of abutment in these abutment zones in operating not only on the natural zones of abutment but also on the zones of the body which, normally, do not serve for abutment of this as for example the back of the knees and in ensuring a distribution of the weight of the body on a surface such as there is no pain, which permits access to a real dynamic treatment of the bed sore and to a real dynamic prevention of bed sores. It also becomes easy to place and then hold, momentarily, the user in a desired position for example for washing or for changing the bed linen, or again for an examination or for nursing. In the case of a surgical mattress, it is possible to thus place the body of a patient in the posture most adapted to the surgical operation to be carried out whilst ensuring an optimum holding thanks to the rigidity which the shell has resulting from the fluid tight enclosure which it has internally being at a pressure held below ambient pressure. In one or the other case, the comfort of the mattress or the cushion remains the optimum despite the rigidity of the shell in so far as this is molded directly to the body whilst the said fluid tight enclosure is at ambient pressure, and this in conditions ensuring an equal redistribution of the abutment pressures with respect to each example of the fluid tight internal chamber or tube. In such applications, it is also possible to cause circulation, in one at least of the examples of the fluid tight internal chamber of a liquid or gel brought to a predetermined temperature for, according to requirements, heating or cooling certain parts of the body.

The fluid tight internal chamber, or respectively at least one of the examples, is removable from the rigid shell, which facilitates manufacture of the device or its repair in case of damage and, further, permits replacement of a fluid tight internal chamber, or respectively an example of the fluid tight internal chambers, intended to contain a predetermined material, by a fluid tight internal chamber or an example of the fluid tight internal chambers more particularly adapted to contain another predetermined material as a function of the particular needs in the applications to the production of reservoirs or of devices for holding and/or support of the human body.

Similarly, according to the applications to which the device of the invention is intended, this can have certain of the following characteristics:

It can comprise a flexible cover enclosing the rigid shell outside the said internal volume, particularly in the case of applications of the present invention to the production of anti-bed sore cushions or mattresses or surgical mattresses. In the case of an application to the holding and/or support of the human body, this cover can advantageously be comparatively inextensible in a zone corresponding to the peripheral zone and comparatively elastically extensible in a zone corresponding to the upper zone, respectively for better performing a holding role and for better adapting to the shape of the user when the fluid tight enclosure is at ambient pressure. Further it can have any suitable disposition for increasing the contact comfort for the use and particularly any cover and/or any appropriate texture. In particular, it can have particularly in its zone corresponding to the upper zone the form of a multi-layer material made by any appropriate process, and for example, by thermal compression welding of several layers of flexible comparatively incompressible material between which is inserted a layer of flexible comparatively elastically compressible material.

The rigid shell integrally encloses, in a continuous manner, the internal volume, which can be the case for example in an application to a reservoir of which the rigid shell is not exposed to shocks or frictions liable to damage its fluid tight walls.

On the contrary, the rigid shell has edges delimiting a localized discontinuity of this rigid shell in which case the edges are either mutually adjoined, so that the rigid shell integrally surrounds the internal volume, and means for mutual assembly of the edges can be provided, or mutually spaced, in which case the rigid shell encloses partially, in a discontinuous manner, the internal volume and means for mutual connection of these mutually spaced edges can be provided. These means of mutual connection can have several methods of practical production according to the end use of the device according to the invention. They can be carried by the edges or be carried and/or constituted by the above mentioned flexible cover when such a cover is provided and, according to the case, can be elastically deformably in extension and/or in torsion and/or in flexure between the edges, or again be elastically deformable in compression. In the case of an application to the production of an anti-bed sore mattress or cushion, or of a surgical mattress, these connection means can comprise at least one flexible connection, deformable both in extension and torsion and flexure between the edges whereas in an application to the production of a floating and/or sliding device or of a reservoir exposed to shocks or to localized fretting, they can be in the form of a wall, complementing the rigid shell for delimiting the internal volume in a continuous manner, in practice in the form of a lower wall of the device if it acts as a floating and/or sliding device or again in a discontinuous manner and for example in the form of an annular wall delimiting an aperture for the passage of a mast in the case of such a device. Such means for mutual connection of the mutually spaced edges can also be omitted in certain applications, for example in the application to a device for the holding and/or support of at least one object in a space such as a piece of baggage, a container, the luggage compartment of a vehicle.

The rigid shell itself can be protected against shocks and/or frettings by appropriate protection means, localized or not, placed next to the shell outside the internal volume and carried by the shell itself or again carried and/or constituted by the mentioned cover when such a cover is provided. These protection means can particularly comprise at least one flexible wall delimiting an external fluid tight chamber placed at over-pressure with respect to ambient pressure, or again a cushion of cellular material. One can provide such protection means in the form of a fender in the case of application of the device according to the invention as a float or hull of a boat, in which case it acts to protect the float or the hull against shocks and/or lateral frettings but, for example in the case of the production of a hull of a boat, one can provide such means for protecting a user from shocks and/or frettings against the rigid shell for example in localizing them in a zone of the rigid shell forming a seat for the user as well as in the case of production of a piece of baggage in the form of a rucksack, such means can be provided for protecting the back of the user against frettings.

In the case of an application to production of an antibed sore mattress or cushion or of a surgical mattress, one can also provide such means for increasing the contact comfort with the user, particularly in the form of an external fluid tight chamber placed next to the rigid shell outside the internal volume and containing a fluid material chosen within the group comprising gasses, gels, liquids, particulate materials, for example placed at a pressure substantially identical to or gain substantially above ambient pressure and which can if desired be made to circulate for example for establishing thermal control of the body of the user and/or thanks to which there can be created a massaging effect in an embodiment according to which the external chamber is provided in several examples and means are provided for establishing in a predetermined manner, thanks to an automatic control, respective predetermined variable pressures in each of the said examples. The fluid tight external chamber or each example of this can be carried directly by the rigid shell itself or be carried and/or constituted by the possible flexible cover.

Although, in numerous applications of the device according to the invention the fluid tight chamber, possible provided in several examples, integrally occupies the internal volume of the rigid shell, one can also provide for certain applications that the device comprises means defining a determined relief inside the said internal volume and preferably removable. This for example is the case when there is produced according to the present invention a surgical mattress, in which there is inserted a substantially incompressible block or on the contrary a block offering a known, chosen compressibility and for example a pneumatic block. When, as is preferred in the case of such an application and as has been indicated above, the rigid shell has mutually spaced edges delimiting a localized discontinuity of this rigid cell, particularly in a lower zone of the shell, and when mutual connection means are provided for the mutually spaced edges these mutual connection means can advantageously have at least one localized projection inside the said internal volume, this localized projection being able to be in contact with a localized zone of the rigid shell, in practice an upper localized zone of this for constituting a mutual localized abutment of the rigid shell and means for mutual connection, themselves superimposed in abutment on a support such as an operating table. In a general manner in numerous applications of the present invention, one can provide one or more localized projections inside the internal volume of the rigid shell, either for giving this a basic shape in the case, for example, where a damage will have caused loss of its rigidity and will lead also to a loss of fluid tightness of the fluid tight internal chamber or certain examples of this, or for permitting limitation of the volumes of fluid displaced for filling or emptying this fluid tight chamber when its essential function is not a storage function, for example so that these volumes approximately equal the volumes of gas or gaseous mixture or liquid which it is necessary respectively to extract from the fluid tight enclosure for rigidifying it or to introduce into the fluid tight enclosure to make it lose its rigidity, which permits carrying out by transfer of fluid between the fluid tight internal chamber and the fluid tight enclosure the shaping of this and its rigidification or its reshaping. Thus, there can be produced according to the invention a cushion of which an upper part is constituted by the rigid shell and the lower part by a rigid or semi-rigid wall delimiting with the shell an internal volume forming an inflatable fluid tight chamber, and provide on this wall inside the said internal volume, hollows and reliefs of anatomical form preserving a certain comfort to the user in the case of such damage. Complementarily, or as a variant, the fluid tight internal chamber can also contain an expansible material totally or partially filling it, wherein this material can be elastically compressible and for example provided for totally filling the fluid tight internal chamber and thus contribute to the shape of the shell when this latter is in its flexible state, or substantially incompressible and provided for partially filling the fluid tight chamber and to thus limit the quantities of fluid to be transferred respectively for filling it or emptying it when its essential function is not a function of storage or for thus giving to the device a predetermined, basic, shape when the shell is in flexible state and the fluid tight chamber is opened to free air, accidentally or at will.

Other characteristics and advantages of a device according to the invention will appear from the following description, in connection with several non-limitative embodiments of such a device, as well as from the accompanying drawings, which form an integral part of this description.

BRIEF DESCRIPTION OF THE DRAWINGS

FIG. 1 shows a perspective partially sectioned view of a reservoir produced in accordance with the present invention.

FIG. 2 shows a view, on a larger scale, of a detail referenced II in FIG. 1.

FIG. 3 shows a view, analogous to that of FIG. 1, of a float produced according to the present invention.

FIG. 4 shows a perspective, partially sectioned view of a hull of a boat produced according to the present invention.

FIG. 5 shows, in a view analogous to that of FIG. 1, an anti-bed sore mattress produced according to the present invention.

FIG. 7 shows, in a view analogous to that of FIG. 1, another embodiment of an anti-bed sore mattress produced according to the present invention.

FIG. 8 shows a view of this other embodiment of an anti-bed sore mattress according to the invention, in section on a plane constituting for this mattress a plane of longitudinal symmetry, referenced VIII—VIII in FIG. 7.

FIG. 9 shows, in a view analogous to that of FIG. 1, a seat cushion produced according to the present invention.

DETAILED DESCRIPTION OF THE INVENTION

Figure 6:
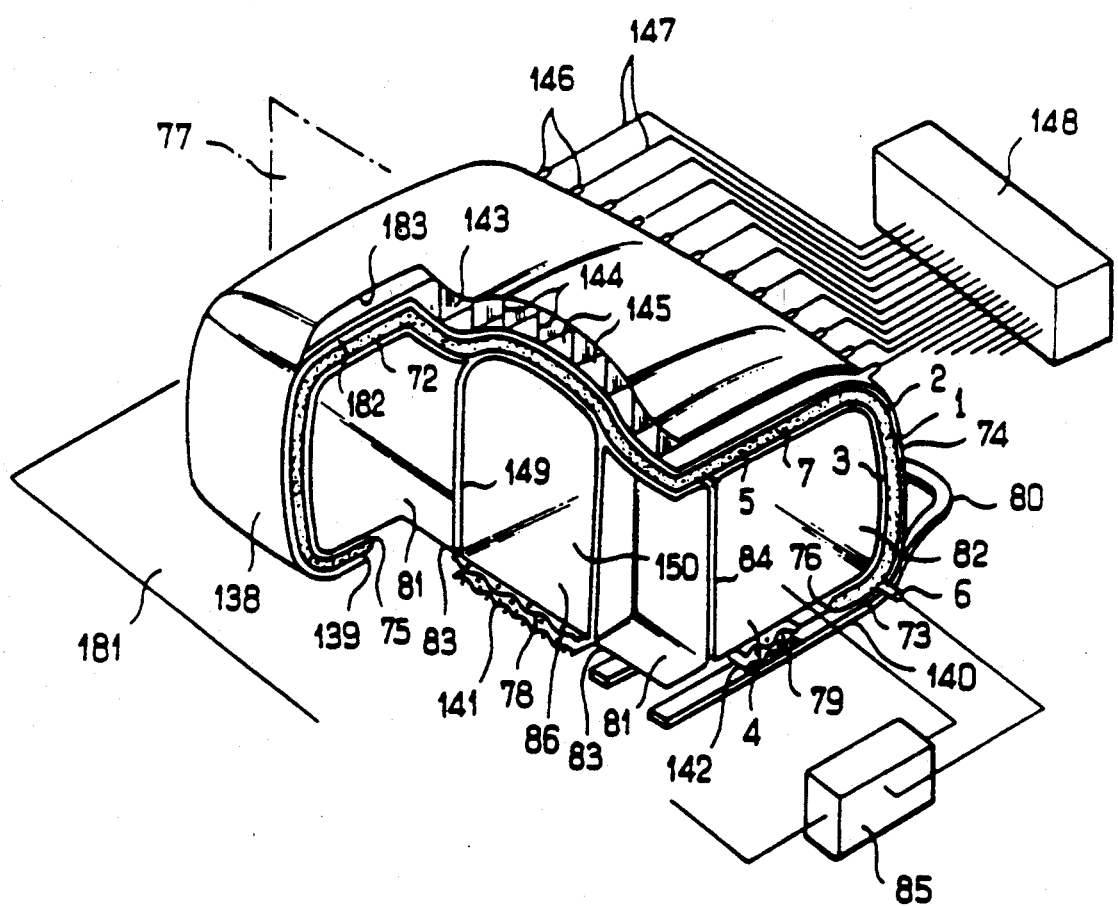
FIG. 6 shows, in a view analogous to that of FIG. 1, a surgical mattress produced according to the present invention.

In all these figures, there is designated by 1 the rigid shell of the device according to the invention, formed from two flexible fluid tight walls 2,3 respectively facing the outside of the rigid shell 1 and the inside of this, that is to say facing an internal volume 4 which the rigid shell encloses at least substantially (FIGS. 3,4,6,7,8,9, 10,11), or indeed totally (FIGS. 1,5). The two flexible, fluid tight walls 2,3 delimit between themselves a fluid tight enclosure held at a pressure below ambient pressure, that is to say atmospheric pressure to which the wall 2 is submitted outside the rigid shell 1, and the pressure to which the wall 3 is submitted inside the rigid shell 1.

The fluid tight enclosure 5, accessible via a value 6 permitting the establishment or re-establishment of this depression or, possibly, placing of the enclosure 5 at ambient pressure, is completely filled with filling material 7 which, in a characteristic manner, has a rigid state whilst it is imprisoned between the two walls 2,3 and the fluid tight enclosure 5 is placed at pressure below ambient, for giving its rigidity to the shell 1, whilst it has a flexible state and gives such flexibility to the rigid shell 1 if the fluid tight enclosure 5 is placed at ambient pressure. This filling material consists for example, as shown in FIG. 2, of a granular material 8 which can be chosen amongst the materials indicated in the mentioned WO 87/06209 or again be of another nature, this granular material 8 being secured inside the fluid tight enclosure 5 by means such as a partitioning 9 forming a fluid tight array for gases or liquids but impermeable to the granular material, as WO 87/06209 teaches, so that when the fluid tight enclosure 5 is ambient pressure either during the manufacture of the rigid shell 1, or when it is later desired to change the shape of it, the granular material preserves inside the fluid tight enclosure 5 a predetermined distribution, that is to say it does not accumulate in certain zones of the fluid tight enclosure 5 to the detriment of other zones of these. This permits preserving between the two walls 2 and 3 of the rigid shell 1 a predetermined spacing when the fluid tight enclosure is drawn down to a pressure below ambient. In all the embodiments of the invention which have been illustrated, this spacing appears substantially constant, it being intended that the scope of the invention will not be departed from by providing a different spacing along the zones of the rigid shell 1.

According to the application of the device in accordance with the invention, the internal volume 4 of the rigid shell I is at least partially filled from at least one fluid tight chamber delimited by fluid tight walls preferably independent of the walls 2 and 3 of the rigid shell 1, and preferably mutually independent when this chamber is provided in several examples, as will appear from the following description of different embodiments of the invention illustrated in FIGS. 1 to 9.

Reference will be made first to FIGS. 1 and 2, where there is illustrated the rigid shell 1 in the form of an elongate tube of revolution about a longitudinal axis 10 and integrally enclosing, in a continuous manner, the internal volume 4. The walls 2 and 3 have in this case a shape which is substantially circularly cylindrical about the axis 10, except in two end zones such as 11 in which the walls 2 and 3 have approximately hemispherical shapes.

Preferably, as illustrated by chain dotted lines, a flexible cover 133 integrally encloses the rigid shell 1 externally, that is to say, in contact with the wall 2, in order to protect this from the risks of tearing. This cover 133 is preferably elastically extensible, and tensioned when the shell 1 is in its rigid state to tightly take the shape of the wall 2.

Internally, the internal volume 4 of the rigid shell I is sub-divided into three longitudinal, fluid tight chambers 12, 13, 14 of which each is delimited by its own fluid tight, flexible walls, respectively 15, 16, 17 and has its own access valve 18, 19, 20 crossing in a fluid tight manner the two walls 2 and 3 of the rigid shell 1 as well as the fluid tight enclosure 5 and the filling material 7 housed in this. Preferably, the walls 15, 16, 17 are elastically extensible whilst, in a general sense, this quality is not required in the walls 2 and 3 of the rigid shell 1. In a manner not shown but easily conceivable by a man skilled in the art, the chambers 12, 13, 14 can be rendered interchangeable by providing in a localized zone of the shell 1 and of the possible cover 133 an opening around which the walls 2 and 3 are mutually joined in a continuous and fluid tight-manner and which permits extraction or introduction at will of one or more of the walls 15, 16, 17.

The chambers 13 and 14 are intended to receive a fluid to be stored such as a liquid or a gas, or again a particulate material, for example cereals, rice or other feed or non-feed grain materials, if the valves 19 and 20 are replaced by devices permitting passage of such material, whilst the chamber 12 is intended to receive a control fluid serving, at will, to create a suction or delivery effect for the fluid stored in the chambers 13 and 14.

More precisely, in connecting the valve 18 to means 21 for suction or delivery, at will, of a control fluid which can be air, or any gas, or gaseous mixture or any appropriate liquid, one can create an initial state of the reservoir in which the chamber 12 filled with control fluid entirely occupies the internal volume 41 the empty chambers volume 4. If, then, one connects the valves 19 and 20 to a source of fluid to be stored, as for example an intermediate storage reservoir, one can create a suction in the chamber 12 by the means 21 causing a progressive reduction of the volume of this chamber 12, accompanied by a progressive increase of the volume of the chambers 13 and 14 and thus create an effect for suction of the fluid coming from the source 22, into the chambers 13 and 14 which progressively fill with this fluid. FIG. 1 illustrates an intermediate state of this progressive emptying of the chamber 12 accompanied by a simultaneous filling of the chambers 13 and 14. When the chambers 12 has been totally emptied of control fluid by the means 21, the chambers 13 and 14 totally occupy, together, the volume 4 and the reservoir is full. The valves 18, 19 and 20 being closed and their respective connections with the means 21 and with the source 22 being cut out, the full reservoir can be stored and transported.

It should be noted that when the fluid to be stored is a liquid, the fact of providing for its reception in several chambers, in practice the chambers 13 and 14, permits the avoidance of any surging of this liquid in the course of transport. When the liquid to be stored is a particulate material, this effect can be reinforced if, after having filled the chambers 13 and 14 with this material, one introduces via the means 21 a control fluid under pressure into the chamber 12 and one evacuates the chambers 13 and 14 by connecting them to a vacuum source substituting the source 22. Further, whatever the nature of the fluid to be stored, such a subdivision increases the safety of use of the reservoir, as is known in a general manner in the field of reservoirs.

When, later, it is desired to draw off the fluid stored in the chambers 13 and 14, one can if one wishes, cause a forced expulsion of this fluid by opening the valves 19 and 20, possibly connected to a device utilizing this fluid, and reconnecting the valve 18 to the means 21, then used for introducing a control fluid under pressure into the chamber 12, which causes the progressive expansion of this latter until it occupies the entire internal volume 4, and as a result reduces progressively the volume of the chambers 13 and 14. If the fluid stored in the chambers 13 and 14 is of a type able to empty on its own from the chambers 13 and 14, it suffices to open the chamber 12 to free air if the control fluid is air or to a reservoir of control fluid in the case of a different nature of this, and the filling of the chamber 12 occurs naturally during the natural emptying of the chambers 13 and 14.

Naturally, in place of simultaneous filling and then simultaneous emptying, the chambers 13 and 14 can be filled successively, then emptied successively in the manner described.

A man skilled in the art will easily understand that the reservoir illustrated in FIGS. 1 and 2 can be used not only for temporary storing of a fluid, but also in other uses and for example by way of ballast in a bathyscaph.

A man skilled in the art will also understand that the number of fluid tight chambers inside the internal volume 4 can be different from three and that particularly one can substitute at the chamber 12 or at the chambers 13 and 14, with the same function and the same connection to the means 20 or 21 respectively, the internal volume 4 itself delimited in a fluid tight manner, or again provide inside the internal volume 4 a single fluid tight chamber entirely filling this volume and possibly delimited by the wall 3 of the fluid tight enclosure 5 itself, with an emptying valve and a vent, for permitting its use in the manner of a traditional rigid cistern.

FIG. 3 will now be referred to, in which there is illustrated a float produced according to the present invention.

This float has the shape of an elongate spindle, with a longitudinal axis 23 arranged horizontally in a use position in which the float is shown in FIG. 3.

In the case of this embodiment of the invention, the rigid shell 1 encloses the internal volume 4 in a continuous manner throughout, except towards the bottom, that is to say in a lower zone 24 of the float. In this lower zone 24, the rigid shell 1 has two longitudinal edges 25, 26 mutually spaced through the majority of the longitudinal dimension of the float and mutually connected in the two end zones such as 27 of this. These two edges 25 and 26 are mutually connected, in a continuous and fluid tight manner, to a fluid tight wall 28 which thus cooperates with the shell 1 for enclosing totally, in a fluid tight manner the internal volume 4.

The wall 28 can be rigid but is preferably elastically deformable in compression, flexure and torsion. Nevertheless, it has a resistance to shocks, frettings and to tearing, greater than that of the shell 1 if it is it which comes in contact with the water or possibly the sea bed. The edges 25 and 26 are positioned approximately at the water line. Above this, a cover 134, in all respects comparable to the cover 133 except that it itself has at the level of the edges 25 and 26 two edges by which it is fixed in a continuous manner to the shell 1 and to the wall 28, can be provided for protecting the wall 2 of the rigid shell 1, which it tightly takes the shape of, against tearing.

The float illustrated in FIG. 3 has in addition an integral fender 29, locally provided in a longitudinal zone of the side 30 of the shell 1, outside the internal volume 4 of this. This finder 29 has the form of a flexible, fluid tight wall 31 having a periphery 32 by which it is fixed in a fluid tight manner to the wall 2 of the shell 1 or to the cover 134 in a manner to delimit with this wall 2 or with the cover 134, respectively, a fluid tight chamber 33 accessible via a valve 34 permitting the introduction into it of a fluid under pressure such as air under pressure, in a manner to inflate the chamber 33. For this, the membrane 31 can be chosen to be inextensible, but sufficiently loose inside its periphery 32 to permit the inflation of the chamber 33, or again be chosen with an elastically extensible nature. Other embodiments of such a fender can be provided, for example in the form of a cushion of cellular, elastically compressible material placed next to the shell 1 or to the cover 134 and made rigid with the shell 1 or the cover 134, respectively.

It will be noted that the wall 28 of the lower zone 24 of the float complements the wall 3 of the rigid shell 1 for delimiting in a fluid tight manner the internal volume 4 of this, so that this internal volume itself constitutes a fluid tight chamber accessible via a valve 35 permitting introduction to it for example of a gas or gaseous mixture such as air at a pressure close to ambient, that is to say atmospheric pressure, preferably at alight over-pressure, without the value of this over-pressure reaching the values which it is necessary to reach in the case of inflatable floats, or again at substantial over-pressure with respect to ambient pressure for contributing the gaseous filling of the internal volume 4 to the rigidity of the assembly of the float. One can also provide a filling of the internal volume 4 by means of a particulate material of relative density less than 1, or of an expanded material, it being intended that this choice can be made independently of any necessity to rigidify the float in its entirety, of which the rigidity can result exclusively from that of the shell 1, resulting itself from the compression of the filling material 7 between the walls 2 and 3 of the fluid tight chamber 5 held at pressure below ambient.

In variants of the embodiment of the float illustrated in FIG. 3, one can however provide that the internal volume 4 of the rigid shell 1 is compartmentalized in a fluid tight manner, by walls there delimiting fluid tight chambers in the manner in which the walls 15, 16, 17 delimit the fluid tight chambers 12, 13, 14 in the case of the reservoir illustrated in FIG. 1 particularly in order to ensure flotation of the float itself in the case of serious damage, leading to perforation of the rigid shell 1 and loss of rigidity of this by the fluid tight enclosure 5 coming to ambient pressure.

A man skilled in the art will easily understand that the design of the float illustrated in FIG. 3 can be changed to various types of floating or sliding devices, as for example sail boards, -hulls of boats and particularly of kayaks, toboggans or skis, of which the wall 28, locally provided in the lower zone 24, constitutes a wear sole and on which means analogous to the fender 29 can constitute protection for the users against shocks. In accordance with the particular case, the wall 28 can be chosen to be more or less elastically deformable in torsion and/or flexure and in compression, whilst nevertheless preferably remaining generally inextensible between the edges 25, 26 of the shell 21.

FIG. 4 shows in detail an adaption of the structure illustrated in FIG. 3 to the case of production of a boat, it being understood that a man skilled in the art will easily be able to deduce an adaption to the production of a toboggan.

The shell 1 will be found again in this case, which forms an upper deck zone 36 of a generally flat and horizontal shape with reference to the use position of the boat, as well as side zones 37 and rear transom zone 38 which substantially surround the deck zone 36 and are terminated downwards, in the region of the waterline, by edges 39, 40 by which the shell 1 is fixed in a continuous fluid tight manner with a bottom wall 41 in all respects comparable to the wall 28 of the float illustrated in FIG. 3. This bottom wall 41 delimits in a fluid tight manner the internal volume 4 of the shell 1, cooperating for this with the side zones 37, the transom zone 38 and the deck zone 36 which are themselves continuous and mutually connected in a continuous manner. This internal volume 4 can thus itself constitute a fluid tight chamber, accessible via a valve 42 permitting the introduction there of a gas or gaseous mixture such as air at a pressure close to atmospheric pressure, and preferably at slight overpressure, or a gas or gaseous mixture such as air at a substantial overpressure with respect to atmospheric pressure, or again any appropriate filling material, particularly expanded material, having a relative density less than one. As was in the case of the float illustrated in FIG. 3, the internal volume 4 can however be sub-divided by flexible partitions such as 43 there defining fluid tight chambers such as 44 of which each can be provided with its own valve 45 permitting the introduction into it of such gas or gaseous mixture or other filling material of relative density less than one.

In a particularly advantageous manner, the deck zone 36 can have hollows and/or reliefs facilitating the seating of a user and as illustrated in FIG. 4 a hollow zone 46 forming a foot-hold, it being intended that another analogous zone is provided in a manner not visible in this Figure, in a bow zone of the boat, and a hollow seat forming zone 47 in a stern zone of the boat. In this hollow zone 47, the shell 1 carries in a fixed manner a cushion 48 made in the manner of the fender 29 of the float illustrated in FIG. 3, in the form of a flexible, extensible or not, fluid tight wall 49 having a periphery 51 along the length of which it is fixed in a continuous fluid tight manner to the wall 2 of the shell 1 in a manner to delimit with this wall 2 a fluid tight chamber 52 accessible by a valve 53 for its inflation by the introduction of a gas or appropriate gaseous mixture, at overpressure with respect to ambient pressure, or again by means of a gel or elastically compressible cellular material increasing the comfort of the seat forming zone 47.

Further, the deck zone can have locally inserted elements about which the walls 2 and 3 are mutually fixed, in a continuous fluid tight manner, as for example an annular, rigid piece 135 provided between the two foot-hold zones such as 46 and intended to permit crossing of the shell 1 by a mast (not shown) and the holding of this mast, which additionally is received in a projection in the form of a sleeve 136 which the wall 41 has projecting inside the internal volume 4. If this is intended itself to constitute a fluid tight chamber, it is necessary to ensure fluid tightness between the piece 135 and the sleeve 136. If fluid tight chambers 44 are defined in the volume 4 by partitions 43, it is necessary to arrange these in a manner to leave a passage for the mast between the piece 135 and the sleeve 136.

Naturally, in a non-shown manner, the boat illustrated in FIG. 4 can comprise for the protection of the shell 1 a flexible cover in all respects comparable to the cover 134 and able to carry the mentioned cushion 148. This cover will have a localized interruption opposite the piece 135. Further, in a non illustrated variant, the deck zone can be defined totally or in part not by the shell 1 but by a deck wall in all respect analogous to the bottom wall 41, and to which it will be connected by the shell 1 then limited to the side zones 37 and the rear transom zone 38. The connection of the deck wall and the bottom wall to the shell 1 thus limited is effected as described in connection with the base wall 41 to the shell 1 of the boat illustrated in FIG. 4 and the wall thus defining the deck zone 36 will have all the arrangements described in connection with this, such as hollow foothold forming zones, a passage for the mast, and a cushion 48, in a manner easily understood by a man skilled in the art. Naturally, such a structure having several walls analogous to the wall of the boat illustrated in FIG. 4 and a shell analogous to the shell 1, or several shells analogous to the shell 1, for delimiting an internal volume 4 housing at least one fluid tight chamber can be found in other fields of application of the present invention, and for example in application to the production of reservoirs or of floats, these examples not being limiting.

It will be noted that in the case of application of the invention to the production of floating devices such as the float illustrated in FIG. 3 or the boat illustrated in FIG. 4 it is not indispensable that the internal volume 4 or the chambers such as 44 arranged in this are filled with a material providing floatation in the case of accident, this role can come from the filling material 7 in the fluid tight chamber 5 while, in the case of tearing of the wall 2 this material is retained, for example by the array of partitions 9 if this is a granular material 8 as illustrated in FIG. 2. This is true, for example, when a granular material is used in the form of hollow balls, fluid tight to gas, of expanded material such as expanded polystyrene. Then, it is possible to ensure the filling of the internal volume 4 constituting itself a fluid tight chamber or the fluid tight chambers 44 arranged in this internal volume exclusively with air at alight over-pressure with respect to atmospheric pressure, which permits setting up then use of a float or of a boat, or other possible sliding or floating device as has been described with reference to FIGS. 3 and 4 in the following manner.

For setting up, after having assembled the walls 2, 3, 28 or 41 and providing between the walls 2 and 3 the filling material 7, and after having also assembled to the wall 2 the possible walls such as 31 and 49 intended to delimit with them inflatable fluid tight chambers such as 33 and 52, one begins by leaving open to free air via the valve 6 the internal chamber 5 of the shell 1 and, by the valves 35 or 42 or by the valves 45, one injects into the internal volume 4 or the chambers 44, respectively, the desired fluid material such as air at slight over-pressure with respect to ambient air so that the shell 1 takes its use shape, such as is illustrated in FIG. 3 or in FIG. 4 for example. It will be noted that it is possible to modify this use shape by providing a temporary contact with the shell 1, from outside, with appropriate shaping means, such as, for example, a mould in the case of a reservoir or of a float or the body of a user in use position in the case of a hull of a boat or of a toboggan. Then, via the valve 6, the fluid tight enclosure is drawn down to a pressure less than that of ambient air, which firmly places the two walls 2 and 3 against the filling material 7 and rigidifies this, that is to say the shell 1 in its entirety. One can then inflate the possibly provided inflatable chambers outside the shell such as the chamber 33 and the chamber 52.

Then, it is possible to reduce the volume of the device when it is not being used, by re-establishing atmospheric pressure inside the enclosure 5 and emptying the internal volume 4 or the chambers 44, respectively, which permits folding of the float, boat or other floating or sliding device into a reduced volume. Naturally it is necessary to preliminarily deflate again the chambers such as 33 and 52, external to the shell 1.

Then, for another use, the initial operations can be repeated to form and then rigidify the shell 1 and inflate the chambers such as 53 and 52.

The reservoir illustrated in FIG. 1 can be shaped in the same way, by inflation of the chamber 12 and, possibly the chambers 13 and 14, while the enclosure 5 is open to free air then drawing down to pressure below ambient this fluid tight chamber 5. The chamber 12, 13, 14 can then be made ready for their respective functions of receiving a control fluid and receiving a fluid to be stored.

Referring now to FIG. 5, there is illustrated a device according to the invention in the form of an anti-bed sore mattress of elongate shape, of which the shell 1 has two mutually parallel, respectively upper and lower flat zones 54, 55 having respective peripheries 56, 57 along the length of which they are mutually connected by a peripheral flank zone or skirt 58. In the state of the device illustrated in FIG. 5, the zones 54 and 55 as well as the zone 58 have a symmetry with respect to a vertical longitudinal plane 71 when the device is in use, but as will appear below this symmetry is only temporary.

Preferably, while the flexible walls 2 and 3 of the shell 1 are substantially inextensible in their zones corresponding to the lower zone 5 and to the peripheral side zone 58, they are elastically extensible in their zone corresponding to the zone 54, in a manner to permit better molding of the shell 1 to the body of the user as will appear below. Similarly, one can choose in accordance with the zones filling materials 7 offering different characteristics, such a choice being also able to be applied, in accordance with needs, to any embodiment of the invention.

As with the shell 1 of the embodiments described with reference to FIGS. 3 and 4 the shell 1 of this embodiment of the invention has a discontinuity localized in its lower zone 55 and more precisely on the plans 71 along the length of which the shell 56 has two straight edges 59, 60 which are however arranged edge to edge, and connected by mutual connection means such as a sliding closure or straps, in a non-shown manner, so that the shell 1 totally encloses, without apparent discontinuity, the internal volume 4 assuring or not a fluid tightness of this. Naturally, other positions can be chosen for this discontinuity which, in particular, can be situated in the peripheral side zone 58.

Advantageously, the shell 1 is enclosed externally by a flexible cover 137 in intimate contact with its wall 2. This cover is preferably removable and interchangeable, and can for example have for this opposite the mentioned discontinuity of the lower zone 55 a similar discontinuity, closed by means of a sliding closure or straps in a non illustrated manner but easily conceivable by a man skilled in the art. The cover 137 can thus ensure the closure of the shell itself in the region of the edges 59 and 60, replacing the mentioned means for mutual connection of the latter. Naturally, when the flexible walls 2 and 3 have an elastically extensible character in their zone corresponding to the upper zone 54 of the shell 1 and a substantially inextensible character elsewhere, the cover 137 can itself by elastically extensible opposite the zone 54 of the shell 1 while it can be substantially inextensible elsewhere. Such an interchangeable cover permits increasing the hygiene of use of the mattress. It also permits increase of comfort and can have for this, opposite the zone 54 of the shell 1, any appropriate covering and/or any appropriate texture. For example, in a non illustrated manner, it can have in its zone corresponding to the zone 54 of the shell 1 a multi-layer structure known in itself particularly in the field of automotive vehicle seat covers and having a flexible base layer of elastically extensible knitting, placed in contact with the shell 1 via the wall 2 of this, an intermediate layer of semi-rigid cellular material, which is elastically extensible and elastically compressible, as well as permeable to air, and a flexible covering layer of textile material which is elastically extensible and permeable to air and is intended for contact with the user, the layers being mutually assembled by thermal compression welding. Naturally, this example should not be considered as limitative.

Internally, the internal volume 4 of generally flat shape, is entirely occupied by three longitudinal fluid tight chambers 61, 62, 63 delimited by flexible, fluid tight walls respectively 64, 65, 66 which can be inextensible or elastically extensible. The chamber 610 of generally flat shape and orientation generally perpendicular to the plane 71 when the device is arranged as illustrated in FIG. 5, extends along the entire length of the upper zone 54 of the shell 1 inside the internal volume 4. Internally, it is subdivided by flexible, fluid tight partitions 67 parallel to the plane 71 with reference to FIG. 5, in a manner to delimit below the entire zone 54 a serpentine circuit 68 for a heat carrying fluid such as liquid and for example water or a gel, which means 69 for circulation and heating or cooling, external to the shell 1 and connected to the chamber 61 by appropriate valve forming means, not shown, thus cause circulation at a pressure which can be substantially identical to or greater than atmospheric pressure, as described below, for, at will, heating or cooling a patient lying on the upper zone 54 of the shell 1.

Naturally, in place of being extended continuously below the entirety of the upper zone 54 of the shell 1, the chamber 61 can extend in a limited zone only of this, being if necessary complemented by other similar chambers in respect of other parts of the upper zone 54 of the shell 1 and provided with their own means 69. The chamber 61 or each analogous chamber can also be filled with a static fluid such as a liquid, or a gas or gaseous mixture, or a gel, or a particulate material, exclusively playing the role of distribution of pressures, in which case the means 69 will be omitted. The chamber 61 and the means 69 for circulating the heat carrying fluid at a desired temperature can also be omitted without departing from the scope of the present invention. further, the chamber 61 or each chamber 61 can be replaced or complemented by an analogous chamber, possibly associated to analogous means or to the means 69, integrated in the zone of the cover 137 placed opposite the zone 54 of the shell 1, or a part only of this zone of the cover 137, in a manner not illustrated in FIG. 5 but illustrated in FIG. 6 in relation to another embodiment of the invention which will be described below. As will appear from the description of this other embodiment, the or each chamber analogous to the chamber 61 or to each analogous chamber can then not only fulfill the same functions as the previously described chamber 61 or each respectively analogous chamber, but also be used by way of cushion for equal distribution of pressures between the body of the user and the shell 1 particularly after rigidification of this, for increasing comfort, or again by way of massage as will be described below in connection with FIG. 6.

While the chamber 61 is symmetrical with respect to the plane 71 in the illustrated condition of the device, the chambers 62 and 63 are mutually symmetric with respect to this plane with reference to FIG. 5 and each of these has an elongate shape in a manner to extend longitudinally, on one side of the plane 71, between a respectively corresponding half of the chamber 61, a respectively corresponding half of the peripheral side zone or skirt 58 and a respectively corresponding half of the lower zone 55 of the shell 1 respectively to the edge 59 or to the edge 60 of this, which edges 59 and 60 are arranged along the plane 71. While they can be filled with a solid, elastically compressible material such as a cellular material in a simplified version of the mattress illustrated in FIG. 5, the two chambers 62 and 63 enclose a fluid which can be substantially incompressible, that is to say a liquid, or substantially elastically compressible that is to say a gas or gaseous mixture such as air, at over-pressure with respect to atmospheric pressure, and are connected by valve forming means, not shown, to pump means or means for inflation and deflation 70 located outside the shell 1 and permitting the establishment at will and preferably in an automatically controlled manner of any desired pressure in each of these chambers 62 and 63, particularly by the transfer of liquid, gas or gaseous mixture from one to the other. With the pump means 70 are also associated means connected to the valve 60 for access to the fluid tight enclosure 5 for permitting, at will and preferably in a controlled manner the placing of this fluid tight enclosure 5 at atmospheric pressure by allowing to enter into it a fluid such as a gas or gaseous mixture or a liquid, at atmospheric pressure, or returning it to pressure below atmospheric pressure by forced extraction of this fluid in accordance with a cycle which will appear from the description below of use of the mattress which has been described with reference to FIG. 5.

Initially, the two chambers 62 and 63 of this are equi-volumetrically filled with liquid or gas or gaseous mixture brought to the same pressure slightly above atmospheric pressure and the possible chamber 61 is filled with the heat carrying fluid or with the static fluid which it is intended to receive. On the contrary, the enclosure 5 is at atmospheric pressure so that the shell 1 has flexibility.

The mattress rests at its zone 55 on a flat horizontal support and the user lies on its zone 54, in a normal lying position. The zone 54 deforms so that, thanks to the identity of pressures present in the chambers 62 and 63 and by a faithful transmission of pressures between these chambers and the user via the zone 54 of the mattress and via the liquid in the chamber 61, there will be equi-partition of contact pressures between the user and the wall 2 of the shell 1 which is then rigidified by drawing down to pressure below ambient.

After a length of time predetermined via a timer incorporated in the means 70 or under the action of other automatic control means incorporated in the means 70 and responding for example to signals coming from contact pressure transducers distributed on the zone 54 of the shell 1 or on the corresponding zone of the cover 137 in a manner to permanently establish a spectrum of distribution of contact pressures between the body of the user and the mattress for controlling, as a function of the recorded programme, modification of the shape of the zone 54 of the shell 1 appropriate to correct this spectrum of distribution of contact pressures, in a manner predetermined as a function of data of values of contact pressure, of duration and of surface application of contact pressure as well as a history of these dates, in a manner easily conceivable by a man skilled in the art, or again on demand from the user noting localized pain, and thanks to the means 70 one can then re-establish the atmospheric pressure in the fluid tight enclosure 5 then cause a modification of the apparent respective volumes of the chambers 62 and 63 for example by a transfer of liquid, gas or gaseous mixture from one to the other of the chambers 62 and 63, which causes tipping of the zone 54 of the shell 1 and, with it, of the user lain on this zone 54 then one re-establishes a pressure below ambient in the fluid tight enclosure 5 for rigidifying the zone 54 in the new shape. Then, after a time determined by the timer incorporated in the means 70 or under the action of the other means for automatic control, or on demand from the user again noting pain, one can again via the means 70 place the enclosure 5 at atmospheric pressure for giving flexibility to the shell 1, then causing a new modification of the apparent respective volumes of the chambers 62 and 63 by for example a new transfer of liquid, of gas or of gaseous mixture from one to the other of the chambers 62 and 63, however in a direction opposed to the direction of the previous transfer which modifies the position of the user at the same time as that of the zone 54, then one re-establishes the pressure below ambient in the fluid tight enclosure 5 for again rigidifying the shell 1 in its new shape.

Such a cycle can be repeated continuously, preferably in an automated way, which avoids the user always lying on the same parts of the body of the upper zone 54 of the mattress and thus permits avoidance of bed sores. A circulation of fluid in the chamber 61 contributes to the comfort of use of the mattress.

Reference will be made now to FIG. 6, where there is illustrated a mattress according to the invention, intended for surgical use, that is to say to supporting and holding the body of a patient during a surgical operation, as well as before and after this operation.

The shell 1 of this mattress has a shape analogous to that of the mattress illustrated in FIG. 5 and particularly comprises upper 72, lower 73 and peripheral 74 zones in all respect analogous to the zones 54, 55, 58 respectively except that at the zone 73, the shell 1 has a localized discontinuity between the longitudinal mutually spaced edges 75, 76 symmetrical to each other with respect to a longitudinal plane 77 constituting a plane of longitudinal symmetry for each of the zones 72 and 73 as well as for the zone 74, and between transverse edges not visible in FIG. 5, also mutually spaced and themselves respectively symmetrical with respect to the plane 77. This plane 77 is vertical when the mattress is in use, the zone 72 and 73 being themselves horizontal as are the edges 75 and 76.

Nevertheless, the longitudinal edges 75 and 76 are mutually connected by a plurality of transverse flexible connections. 78, preferably elastically extensible, as we II as the transverse edges (not shown) are mutually connected by a plurality of longitudinal flexible connections 79, preferably elastically extensible.

The internal volume 4 of the rigid shell 1 is occupied by a transverse juxtaposition of fluid tight chambers 81, 82 delimited by respective flexible fluid tight walls 83, 84 inextensible or elastically extensible. These chambers 81 and 82 are associated, via the intermediary of non-shown access valves, to means 85 analogous to the means 70 in that they permit the establishment of any desired pressure in one or the other of these chambers and placing of the fluid tight enclosure 5 alternatively at atmospheric pressure or below atmospheric pressure.

Nevertheless, in localized manner inside the volume 4, on certain of the flexible connections 78, 79 there rests preferably freely a transverse projection 86, which can be rigid and substantially incompressible, for example constituted by a rigid approximately parallelepiped block, in a non-shown illustrated manner, or preferably elastically compressible, and for example constituted by a substantially inextensible flexible envelope 149 delimiting a fluid tight chamber 150 analogous to the chambers 81 and 82 and inflated at substantial over-pressure with respect to atmospheric pressure as is illustrated, on which the upper zone 72 of the shell 1 is locally abutted so that it thus benefits from an abutment on any generally flat and horizontal support 181, such as an operating table, on which the lower zone 73 of the shell 1 and its connections 78, 79 re st downwards. Further the projection 86 is enclosed completely by the zones 81 and 82, with respect to which it constitutes for the zone 72 a localized abutment, of predetermined firmness, in a predetermined position by the positioning of the flexible connection to which it is associated for constituting a block.

It can be easily conceived that adjusting in a predetermined manner the pressures in the chambers 81 and 82 surrounding the block constituted by the localized projection 86 as well as in this latter when its nature is that required when the enclosure 5 is at atmospheric pressure one can give to the upper zone 72 of the shell 1 any appropriate shape to place the patient in the best appropriate position then subsequently fix the shell 1 in the position obtained by drawing down below ambient the pressure in the fluid tight chamber 5.

Such a mattress has a significant advantage with respect to other types of mattresses used in surgery, in that the rigidity which it has when the shell 1 is in rigid state, that is to say when the fluid tight enclosure is drawn down below ambient, permits the placing on it of the patient in the required position before placing the mattress on the operating table, then bringing the mattress with the patient onto the operating table without having to move the patient with respect to the mattress, to carry out the operation then, after the operation, taking the patient to the recovery room again without moving him with respect to the mattress. For this, one can advantageously provide on opposite sides of the mattress carrying handles such as 80, for example constituted by the ends of transverse flexible -and substantially, inextensible straps, engaged under the lower zone 73 of the shell 1 and under the flexible connection 78, 79 for example by the intermediary of appropriate loops (not shown) fixed to the wall 2 of the fluid tight enclosure 4.

Naturally, although this has not been shown, the mattress illustrated in FIG. 6 can have, in common with that illustrated in FIG. 5, means analogous to the chamber 61 and permitting the retention of a fluid against its zone 72 or for causing circulation of a heat carrying fluid against this zone 72 before and/or during and/or after the operation, either inside the volume 4, particularly thanks to the presence of at least one chamber analogous to the chamber 61 and interposed between the upper zone 72 of the shell 1, on the one hand and the projection 86 as well as the chambers 81 and 82, on the other hand, or outside the volume 4, and more precisely opposite the zone of the wall 2 corresponding to the zone 72 of the shell 1, thanks to the presence of at least one chamber analogous to the chamber 61 and for example integrated with a flexible cover 138 externally enclosing the shell 1 and tightly fitting the wall 2 of this.

The cover 138, preferably substantially inextensible, has a size analogous to the cover 137 described with reference to FIG. 5 in that it tightly encloses, via the wall 2 of the enclosure 1, the rigid shell 1 in its upper zone 72, its peripheral zone 74 and its lower zone 73, opposite the discontinuity of which it has nevertheless itself a localized discontinuity between two longitudinal edges 139, 140 mutually spaced and symmetric the one with the other with respect to the plane 77 and mutually connected by elastically extensible flexible transverse connections such as 141 and two transverse edges not visible in FIG. 6, mutually spaced from each other, respectively symmetric about the plane 77 and mutually connected by elastically extensible longitudinal flexible connections 142. It will be noted that the straps constituting the carrying handles 80 can be carried by the cover 138, for example via loops (not shown), rather than via the shell 1 itself.

Opposite the entirety or a predetermined part of the upper zone 72 of the shell 1, the cover 138 delimits by two flexible fluid tight walls 182, 183, a fluid tight chamber 143 which, like the chamber 61, has a flat shape and an orientation generally substantially perpendicular to the plane 72 in the illustrated shape of the mattress and can be partitioned like the chamber 61 for receiving a static fluid for distribution of pressure or a circulating heat carrying fluid.

Nevertheless, in the illustrated example, the chamber 143 is partitioned in a fluid tight manner, by transverse flexible partitions 144, into a multitude of transverse, mutually independent, fluid tight chambers 145, which are filled with a fluid such as a liquid or a gas or gaseous mixture and of which each has its own access means in the form of a respective valve 146 connected via a respective conduit 147 to a controller 148 permitting the establishment in accordance with a predetermined sequence of respective predetermined pressures, variable in time in a predetermined manner between maximum values which can be substantially greater than atmospheric pressure and minimum values which can be of the order of atmospheric pressure, in the fluid respectively filling each chamber 145, in order to bring about a massaging effect to the body of the user. Naturally, other means can be utilized for such an action on the pressures existing in the chambers 145 respectively. The massage obtained is the more efficacious since, as the shell 1 is shaped directly to the body of the user in the manner previously described, via the intermediary of the chamber 143 placed at equi-pressure during this shaping, there is established between the body of the user and the mattress a continuous contact such that the variations of pressure in the chambers 145 are faithfully transmitted to the respectively corresponding zones of the body.

Naturally, in place of being built up on the shell 1 via the intermediary of the cover 138, the sub-divided chamber 143 can be arranged directly on the shell 1, for example between the wall 2 and a flexible, fluid tight wall doubling this outside the mattress in the region of the upper zone 72 of the shell 1.

As has been previously described, a sub-divided chamber analogous to the chamber 143 and associated like it with a controller such as the controller 148, permitting the obtaining of a massage effects can be provided as in the case of the mattress illustrated in FIG. 5, either directly on the shell 1 of this, or in the region of its cover 137.

Such a chamber, or again a chamber permitting the receiving of a static fluid for distribution of pressure or a heat carrying fluid circulating as has been described with reference to FIG. 5 either inside the internal volume 4 of the shell 1, or outside this can also advantageously b provided, although this has not be illustrated, in an anti-bed sore mattress which will now be described with reference to FIGS. 7 and 8 and which in addition constitutes a more completed version of the mattress described with reference to FIG. 5.

As is shown in FIGS. 7 and 8 this anti-bed sore mattress has a general symmetry with respect to a vertical longitudinal plane 87 when the mattress rests flat on a preferably rigid flat horizontal surface 88.

The shell 1 of this mattress has a size analogous to that of the she'll 1 of the mattress described with reference to FIG. 6, in that it has an upper zone 89 and a lower zone 90 mutually connected by a peripheral zone 91 and in that, while the zones 89 and 91 are continuous, the zone 90 has a discontinuity delimited by two longitudinal edges 92, 93 mutually spaced and mutually symmetric with respect to the plane 87 and by two mutually spaced transverse edges 94, 95, of which each is symmetric with respect to the plane 87. The two edges 92 and 93 are mutually connected by a plurality of transverse elastically extensible flexible connections 96 between the edges 92 and 93 and the transverse edges 94 and 95 are mutually connected by a plurality of elastically extensible flexible longitudinal connections 97 between them, these flexible connections 96 and 97 being chosen such that they remain tensioned whatever the shape which is given to the shell 1 in the limits of use of the mattress which will be described below.

The shell 1 is preferably enclosed by a flexible cover 151 not detailed but in all respects analogous to the cover 138 particularly as regards its method of enclosing the zones 89, 90, 91 of the mattress, as regards its lower discontinuity between the edges mutually connected by non-shown elastically extensible flexible connections and as regards the fact that it can have the different forms of embodiment described with reference to FIGS. 5 and 6, as regards the covers 137 and 138 respectively and particularly delimit opposite the upper zone 89 of the shell 1 a fluid tight chamber adapted to receive a static pressure distributing fluid or a circulating heat carrying fluid or a fluid permitting the obtaining of a massaging effect.

While the lower zone 90 of the mattress is flat, and rests flat in practice on the support 88, the case being by the intermediary of the cover 138 and elastically extensible flexible connections closing a discontinuity in this, its upper zone 89 has three parts 98, 99, 100 of which each is flat, perpendicular with respect to the plane 87 and symmetric with respect to this in two illustrated shapes, and which follow each other longitudinally from one transverse end zone 101 of the mattress to another transverse end zone 102 of this. These three parts 98, 99, 100 can be arranged on the same median plane parallel to the support 88, for giving the upper surface 89 of the shell 1 a generally flat shape, in a shape of the mattress illustrated in chain dotted lines in FIG. 8. However, thanks to means which will be described below, one can also give the mattress a shape in which the upper zone 89 of the shell 1 has a undulating shape and which is illustrated in full lines in FIGS. 7 and 8. This latter shape will serve for reference to the following description.

Longitudinally, the part 98 of the upper zone 89 of the shell 1 has dimensions such that it can serve for support of a human body with the head at the end zone 101 while the posterior is positioned in a junction part 103 between the parts 98 and 99. This part 98 descends progressively to the end zone 101 at the junction zone 103. Longitudinally, the part 99 ascends from the junction part 103 with the part 98 to a junction part 104 with the part 100 and has dimensions substantially corresponding to those which separate the posterior from the knee for receiving the thighs of the user, while the part 100, descending from the junction part 104 with the part 99 as far as the end zone 102 of the mattress has dimensions corresponding to the dimensions separating the knee from the foot for serving to support the calves and the feet of the user. The concave junction part 103 and the convex junction part 104 have rounded shapes.

As will appear below, the geometry of the different parts 98, 99, 100, 103, 104 of the shell.1 can be modified as a function of the needs.

In the case of this mattress, the internal volume 4 of the shell 1 is occupied by four fluid tight chambers 105, 106, 107, 108 of which each is delimited by a respective preferably elastically extensible, flexible fluid tight wall 109, 110, 111 and 112 and connected via respective valves (not shown) to means for controlled inflation and deflation, to which is also connected the valve 9 for access to the fluid tight enclosure 5 of the shell 1 for functioning as will be described below.

The two fluid tight chambers 105 and 106 have the shape of longitudinal flat tubes mutually juxtaposed transversely immediately below the upper zone 89 of the shell 1 and, in their shape illustrated in FIG. 7, are mutually symmetric in respect of the plane 87. Each of these tubes thus extends transversely from the plane 87 as far as the peripheral zone 91 of the shell 1 and longitudinally from the end zone 101 of the mattress as far as the end zone 102 of this, being juxtaposed in the two zones to the peripheral zone 91 of the shell 1 as appears from examination of FIG. 8, showing the wall 110, it being understood that the wall 109 is symmetrical thereto with respect to the plane 87. The two longitudinal tubes thus constituted are mutually adjoined, via the walls 109 and 110, along the length of the plane 87.

Between the two chambers 105 and 106 and an assembly constituted by the lower zone 90 of the shell 1 and by the straps 96 and 97 are locally interposed the two other chambers 107 and 108, which themselves have the shape of transverse tubes of which the first is localized beneath the part 98 of the upper zone 89 while the second is localized beneath the parts 99, 100 and 104 of this upper zone 89 in order to give to the parts 98, 99, 100 of the upper zone 89 of the shell 1 the shape indicated above. Transversely, the two transverse tubes thus constituted extend symmetrically with respect to the plane 87 for adjoining on each side thereof the peripheral zone 91 of the shell 1. When they are viewed in section on a longitudinal plane, as is the case in FIG. 8, they have a substantially triangular section, that is to say respectively a right angled triangle section of which the hypotenuse lies at the walls 109, 110 of the chambers 105 and 106 while the edges of the right angle lie respectively at the peripheral zone 91 of the shell 1 and the assembly formed by the lower zone 90 of this and by the straps 96, 97, and an isosceles triangle section of which the base lies at this assembly and the two other edges lie at the walls 109 and 110, the apex being arranged below the junction part 104 between the parts 99 and 100 of the upper zone 89 of the shell 1. In the example illustrated, the two chambers 107 and 108 are mutually disjoint below the junction part 103 between the parts 98 and 99 of the upper zone 89 of the shell 1 of the mattress, so that the walls 105 and 106 react directly on the assembly formed by the lower zone 90 of the shell 1 and by the straps 96 and 97 but it can also be provided that, while remaining mutually independent, the chambers 107 and 108 are mutually adjoined below this point 103, or again provide between the chambers 107 and 108 a supplementary transverse chamber, in the form of a transverse tube localized plumb with the part 103, beneath this, and in all respects analogous to the chambers 107 and 108 of which this supplementary chamber will be independent particularly as regards its inflation and deflation by the means 113.

Naturally, one will not depart from the scope of the present invention in reversing the respective positions of the longitudinal and transverse tubes, that is in interposing these latter between the longitudinal tubes and the upper zone 89 of the shell 1.

The functioning of the mattress illustrated in FIGS. 7 and 8 can be the following, it being understood that this functioning can be controlled manually or automatically by the means 113, which can be provided for this with a timer or other control means responding for example to signals coming from contact pressure detectors distributed on the upper zone 89 of the shell 1 for establishing permanently a spectrum of distribution of contact pressure between the body of the user and this zone 89 and for controlling as a function of a recorded program, modifications of the shape of the upper zone 89 of the shell 1 appropriate to correct this spectrum of contact pressures, in a manner determined as a function of data of the values of contact pressure, of duration and of surface of application of contact pressure, as well as of a history of these data.

In a first phase of use of the mattress, corresponding to its being brought into service, the fluid tight chamber of the shell 1 is brought to ambient pressure which gives the shell a flexibility, and the chambers 105, 106, 107, 108 are placed at equi-pressure, then the user lies on the upper surface 89-of the mattress. This upper zone 89 then conforms to the body of the user, in a manner to ensure an equal distribution of pressures, which are faithfully transmitted between the chambers 105 and 106 on the one hand and the body of the user on the other hand. On inflation to a greater or lesser extent, in a possibly different manner, of the chambers 107 and 108, one can orient the different parts 98, 99, 100 of the upper zone of the mattress the one with the other while preserving this equal distribution of pressures. One can thus in particular totally deflate the chambers 107 and 108 for giving the mattress the shape illustrated in chain dotted lines in FIG. 8. When the mattress has the desired shape, the fluid tight chamber 105 is drawn down to pressure below ambient, which rigidifies the shell 1 in the shape obtained. It will be noted that when the shell 1 is in its rigid state, the straps 96 and 97 maintain it in tension around the fluid tight chambers 105, 106, 107, 108.

Then, in an automatic or manually controlled manner, for example in the case of localized pain of the user, one can again place the enclosure 5 at atmospheric pressure for modifying the shape of the upper zone 89 of the shell 1 for example by placing one of the chambers 105, 106 at over-pressure with respect to the other, which causes the symmetry of the zone 89 with respect to the plane 87 to disappear in making it tip with respect to this, or in modifying the respective inflations of the chambers 107 and 108. When a new desired shape is obtained, one again rigidifies the shell 1 placing the fluid tight chamber 5 at pressure below ambient. The reverse operation can then be carried out, as has been explained with respect to FIG. 5.

The recourse to automatic means for controlling the functioning of the mattress permits the managing of statistical distribution with time of abutment zones of the body of the user on the mattress and of mutual contact pressures in these zones, using not only the natural abutment zones of the body but also zones which do not normally serve for abutment, such as the back of the knees for ensuring from this that in each zone of the body, the mutual contact pressure and the duration of application of this pressure are permanently appropriate to avoid not only short term pain, but also the appearance of bed sores over the long term, or again the treatment of preexisting bed sores.

Naturally, while in the different embodiments of a mattress according to the invention which have been described with reference to FIGS. 5 to 8, there has been described an entire filling of the internal fluid tight chambers of the internal volume 4 of the shell 1 with fluid material, it can also be provided that these latter further contain elastically compressible expanded material, in block or particulate form, filling them partially or totally for contributing to the shape of the shell 1 while this is in its flexible state, giving to the mattress a basic shape in such case and when further the internal fluid tight chambers are placed at atmospheric pressure, and limiting the quantities of fluid material to be displaced for respectively filling or emptying these chambers. One can also use for these different effects materials or devices placed directly inside the internal volume 4, and particularly devices of the type described in WO 87/06209 mentioned above, offering in themselves a possibility of shaping at will. Further, while with reference to FIGS. 5 to 8 there have been described only two longitudinal chambers such chambers can be provided in greater number in transversely juxtaposed position.

One can also provide the chambers 62, 63, 81, 82, 105, 106, 107, 108 described with reference to FIGS. 5 to 8 in a different number and in a different shape, and for example in the shape of a plurality of studs mutually juxtaposed both longitudinally and transversely, under the upper zone 54, 72, 89 of the shell 1, for permitting a finer adaption of the shape of the shell 1 to the needs, when the enclosure 5 is at atmospheric pressure, by cooperating for this effect with the means 70, 148, 113 suitably adapted to the number of these chambers and suitable to communicate to each of them any respective desired volume, that is to say any desired dimension perpendicular to the upper zone 54, 72, 89 of the shell 1, by inflation at preferably small over-pressure with respect to atmospheric pressure or deflation, for example as a function of memorized data.

As required, when the internal volume 4 is closed in a fluid tight manner either by mutual fluid tight connection of the edges 59 and 60 of the shell 1 in the case of the embodiment illustrated in FIG. 5, or via any appropriate means such as a fluid tight, elastically extensible sheet connected in a fluid tight, preferably removable manner to the longitudinal edges 75, 76 and to the transverse edges (not shown) in the case of the embodiment illustrated in FIG. 6 or to the longitudinal edges 92, 93 and to the transverse edges 94, 95 in the case of the embodiment illustrated in FIGS. 7 and 8, in a manner not shown but easily conceivable by a man skilled in the art, one can also provide tight adaption of the shape of the shell 1, when the enclosure is at atmospheric pressure, by the drawing down to vacuum of the interior of the interval volume 4, between the wall 3 delimiting the enclosure 5 towards this, on the one hand, and the respective walls 64, 65, 66, 83, 84, 109, 110, 111, 112 of the chambers 61, 62, 63, 81, 82, 105, 106, 107, 108 as well as the projection 86, on the other hand, thanks to the means 70, 148, 113 respectively, then suitably connected for this to the internal volume 4, in a manner not shown but easily conceivable by a man skilled in the art, and suitably controlled for this. To the mentioned cycles of operation will then be added a phase of drawing down of the internal volume 4 between the changing of the shape of the chambers 62, 63, 81, 82, 105, 106, 107, 108 and the drawing down of the enclosure 5, and a phase of establishment of atmospheric pressure in the internal volume 4 at any desired moment since it will be preliminary to a new change of the shape of the chambers.

Similarly, in a simplified version of a mattress according to the invention, there can be provided inside the shell 1 a single inflatable fluid tight chamber as has been described for example in the case of the float illustrated in FIG. 3 or the boat illustrated in FIG. 4.

Nevertheless, in the case of an application of the invention to holding and/or support of the body, it is preferred to limit recourse to such a single internal chamber to the case of devices of lesser dimensions than those of a mattress, that is to say to the case of cushions.

There is illustrated in detail in FIG. 9 a seat cushion which, with reference to its use position, is flat in the vertical direction and symmetrical with respect to a vertical plane 152 and of which the design is related to that of the float illustrated in FIG. 3 in that the rigid shell 1 encloses the internal volume 4 in a continuous manner on all sides, except at the base, that is to say in a lower zone 153 of the cushion in which the rigid shell 1 is connected in a continuous fluid tight manner via an annular edge 154 to a fluid tight wall 155, which is rigid or preferably elastically deformable in compression, flexure and tension and which thus cooperates with the shell 1 for enclosing on all sides, in a fluid tight manner, the internal volume 4. This internal volume 4 thus constitutes itself a fluid tight chamber accessible by a valve 156 permitting introduction into it of a fluid or extraction of the latter, for example a liquid or a gas or a gaseous mixture such as air at a pressure close to ambient, that is to say atmospheric pressures, and preferably at slight over-pressure or again a gel.

In variants of the embodiment of the cushion illustrated in FIG. 9, it can however be provided that the internal volume 4 of the rigid shell 1 is compartmentalized in a fluid tight manner, by walls there delimiting fluid tight chambers, provided with respective access values, in a manner of the walls 15, 16, 17 delimiting the fluid tight chambers 12, 13, 14 in the case of the reservoir illustrated in FIG. 1.

The wall 155, via which the cushion rests on any appropriate support such as a chair or armchair, has underneath, that is to say opposite the internal volume 4, any appropriate shape for this and for example a generally flat shape edged by a convex edge connecting to the shell 1 at the region of the edge 154.

Upwardly, that is to say towards the inside of the internal volume 4, the wall 155 has an anatomical shape, that is to say a relief characterized by a projection 158 localized along the plane 152 between two relatively hollow regions 159, 160 arranged symmetrically with respect to each other and to the plane 152, so that if the chamber constituted by the internal volume 4 is empty and the shell 1 is in its flexible state by introducing atmospheric pressure into the enclosure 5, the user sitting on the wall 155 via the intermediary of the shell 1 in its flexible state is nevertheless positioned in suitable, if not optimum conditions of comfort and held by the cushion. Further, the presence of the projection 158 inside the internal volume 4 permits reduction of the volume of fluid material to be displaced for filling or emptying this and in particular, when this material is a gas or gaseous mixture or again a liquid also used for placing the enclosure 5 at atmospheric pressure by introduction of this material into it or for creating a vacuum in the enclosure 5 by extraction of this material from it, to substantially equilibrate the volumes of fluid material which must respectively be introduced into the volume 4 for inflating this and extracted from the enclosure 5 for rigidifying the shell 1, or extracted from the volume 4 for deflating this and introduced into the enclosure 5 for making the shell 1 flexible, via the intermediary of pump and refilling, or inflation or deflation, means 161 to which are connected the valves 6 and 156.

Such a cushion can be used in the following manner:

When the shell 1 is in a flexible state and the fluid tight chamber defined by the internal volume 4 is inflated with the chosen fluid material, preferably a gas or gaseous mixture or a liquid, the cushion resting by the wall 155 on the support which is intended to receive it, the user is seated in normal position on the shell 1 which hugs him, the material filling the chamber defined by the volume 40 assuring an equal distribution of abutment pressures of the body of the user on the shell 1.

Then the shell 1 is rigidified in the shape obtained, and one can then either maintain in the internal volume 4 the material which previously served to inflate this volume, possibly modifying its pressure by increase or reduction, or extract this material from the internal volume 4, possibly substituting for it another fluid material possibly able later to rigidify or have an elastic compressibility and/or a flexibility, such as for example an expandable synthetic resin.

Externally the cushion is advantageously enclosed, at least opposite the shell 1 which constitutes the part intended to come into contact with the body of the user, with a removable cover 157 for increasing the comfort of contact and use over long duration, and being able to have for this the different characteristics of the covers 137, 138, 151 described with reference to FIGS. 5 to 8.

Naturally, the embodiment of a cushion illustrated in FIG. 9 constitutes only a non-limitative example of a cushion able to be produced in accordance with the present invention and, in particular, one can subdivide the internal volume 4 into several mutually independent fluid tight chambers possibly associated with a controller or means for controlling at will the inflation and deflation of these, as has been described with reference to FIGS. 5 to 8 in the case of a mattress.

Figure 10:
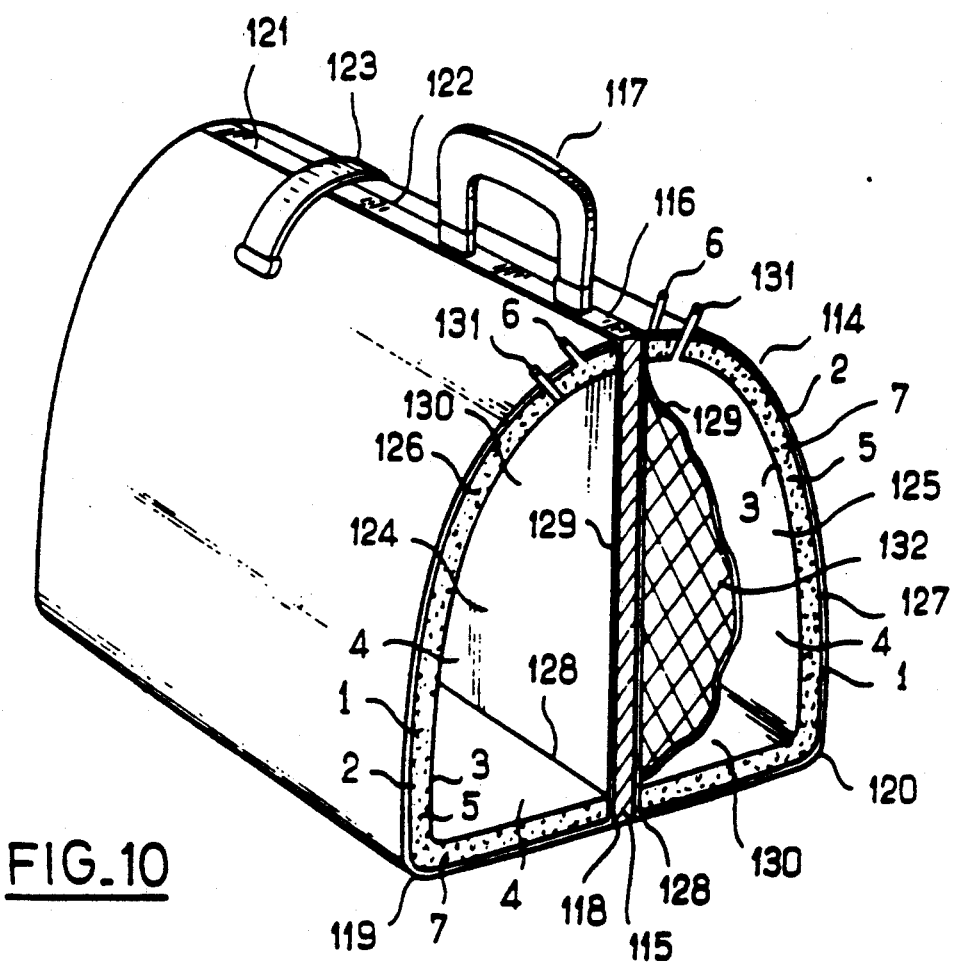
FIG. 10 shows, in a view analogous to that of FIG. 1, a piece of baggage such as a bag equipped with a device for holding and/or support of objects produced according to the present invention.

Referring now to FIG. 10, there is shown in detail the application of the invention to production of a device for holding and support of objects in a piece of baggage, by way of non-limitative example of means defining an internal space in which one may wish to hold one or more objects.

The bag 114 illustrated in FIG. 10 has, with reference to the position illustrated, a flat vertical rigid median wall 115 particularly having an upper horizontal edge 116 provided with a carrying handle 117, and a lower edge 118 also horizontal. Along the bottom edge 118 and two non shown vertical edges of the wall 115 are fixed to this, respectively on one side and the other of this, two lateral walls 119 and 120, flexible in themselves and of enclosure shape, which walls 119 and 120 have a respective upper free edge 121, 122 able to be held against the median wall 115 along the length of the upper edge 116 of this under the action of closure means 123 such as straps provided with locks, for closing the bag, or on the contrary able to be spaced from the upper edge 116 of the wall 115 when one wishes to open the bag. The shape and practical embodiment of the bag 114 is not critical as regards the present invention and can be chosen within a large range of possibilities so that the bag 114 will not be further described.

Each of the side walls 119 and 120 thus delimits with the median wall 115 a respective internal space 124, 125 intended to receive objects.

If the two cavities 124 and 125 are not completely filled with objects, the bag 114 is anesthetically deformed, and the objects which are placed in it can move, collide and risk being damaged.

A device according to the present invention, respectively housed in each of the spaces 124 and 125, and respectively designated by the reference 126 and 127, can avoid these inconveniences.

For this, the shell 1 of each of the devices according to the invention 126, 127 fits at its wall 2 the determined internal contour of the respective lateral wall 119, 120 occupying a corresponding shape to that which it will have if the respective cavity 124, 125 is full, which rigidifies this respective wall 119, 120 in such a shape.

On the contrary, the internal volume 4 of each shell 1 is integrally open towards the median wall 115 of the bag 114, along the length of the edges of which the two walls 2 and 3 of each shell 1 are connected to this wall 115 by a respective peripheral edge 128.

Along the length of this edge 128 it is also connected to the two walls 2 and 3, in a fluid tight manner, an elastically extensible, flexible, tight wall 129, which thus delimits with the wall 3 of the fluid tight enclosure 5, in the internal volume 4 of the device 126 or 127 respectively, a respective fluid tight chamber 130 accessible via a valve 131 traversing the respectively corresponding lateral wall 119, 120, as does the valve 6 for access to the fluid tight enclosure 5 of the shell 1.

When the bag 114 is empty, one can as illustrated with respect to the cavity 124 place the wall 129 in contact with the median wall 115 by opening the fluid tight chamber 130 to free air via the valve 131 and bringing into play the elasticity of the wall 129 or by introducing air at slight over-pressure into the fluid tight chamber 130 via the valve 131. If the two cavities 124 and 125 are empty of objects to be carried, the two devices 126 and 127 according to the invention can be placed in this state.

If, as illustrated in respect of the space 125, one of the spaces 124 and 125, or each of these spaces, is intended to be partially filled with objects to be carried such as 132, these objects are placed in contact with the median all 115 in this cavity such as 125, while open, then this cavity such as 125 is closed by the means 123. In the course of this closure, the wall 129 deforms coming into contact with the objects 132 which it urges against the median wall 115, the valve 131 being open for putting the fluid tight chamber 130 at atmospheric pressure. Then, via the valve 131, there is introduced into the fluid tight chamber 130 air at slight over-pressure with respect to atmospheric pressure, which tightly places the wall 129 on the objects 132 themselves in abutment against the median wall 115, and thus holds these objects inside the bag 114, Naturally, one can practice the same inside the space 124.

The elasticity of the wall 129 is chosen such that it can, if necessary, come into contact against the wall 3 of the enclosure 5 of the shell 1 if the corresponding cavity 124 or 125 is completely filled with objects 132 to be carried, the corresponding chamber 130 then remaining at atmospheric pressure.

When one wishes to retrieve the objects thus housed in the bag 114, one re-establishes via the valve 131 atmospheric pressure in the corresponding chamber 130, then one opens the bag 114 to retrieve the objects 132.

If one wishes to extract the device according to the invention 126 127 from the corresponding space 124, 125, one can via the valve 106 establish atmospheric pressure in the fluid tight enclosure, which makes the shell 1 flexible and thus permits reduction of its volume for taking it out of the bag, and then possibly introducing it there again. Then, for giving back to the shell 1 its shape, one can leave the fluid tight enclosure 5 open to free air via the valve 6 and, after having closed the bag 114, establish a slight over-pressure in the chamber 130, which on the one and places the wall 129 against the median wall 115 of the bag 114 and on the other hand places the shell 1 against the respective side wall 119, 120. Then, the shell 1 is rigidified in the shape obtained by drawing down below ambient the pressure in the fluid tight chamber 5, and then removing the over-pressure in the chamber 130 for then using the bag 114 as has been indicated above.

Naturally, although the bag illustrated in FIG. 10 has two spaces 124 and 125 defined, respectively on the one hand by the rigid median wall 115 and on the other hand by the respective flexible side walls 119, 120, the scope of the present invention will not be departed from by providing a bag having a single flexible side wall, comparable to one of the walls 119 and 120, delimiting a space with a rigid wall comparable to the wall 115 but also lateral, that is to say delimiting the space at the outside of the bag, and providing inside this cavity a device according to the invention, that is to say comparable to one of the devices 126 and 127, and cooperating with the rigid wall and with the flexible wall as each device 126, 127 cooperates with the wall 115 and, respectively one or other of the walls 119, 120.

Figure 11:
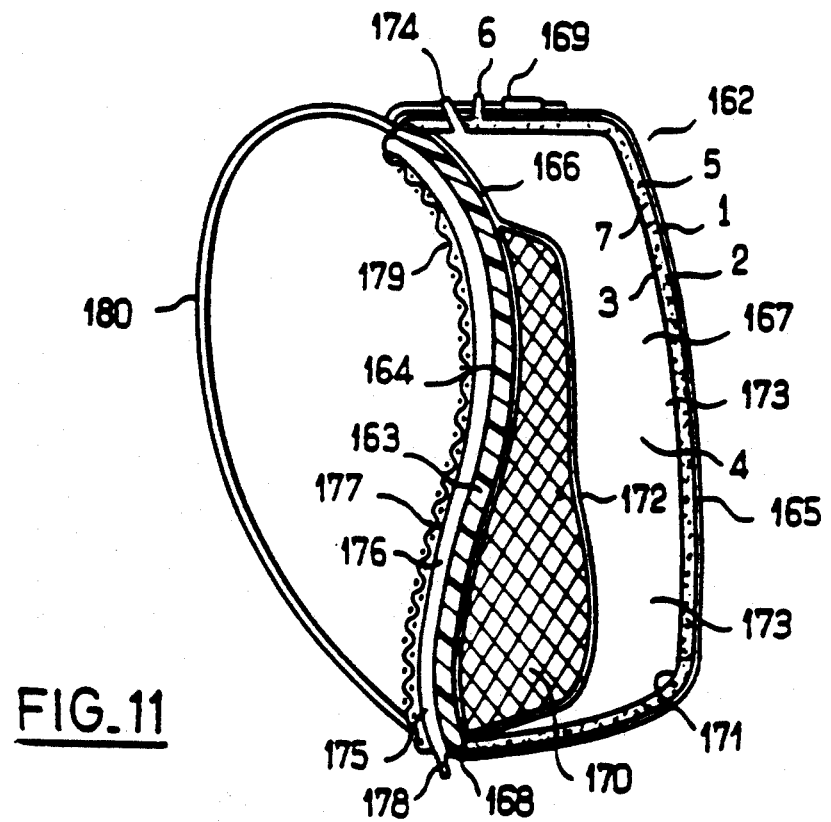
FIG. 11 shows, in a sectional view on a vertical median plane, a rucksack produced according to the present invention.

FIG. 11 illustrates in fact a rucksack 162 having such a concept, that is to say having a rigid or semi-rigid wall 163, of a generally anatomically adapted shape for abutment on the back of a user via a face 164, and a flexible enclosure wall 165 delimiting with another face 166 of the all 163, opposite the face 164, a space 167 in a manner of which one of the flexible walls 119, 120 of the bag 114 illustrated in FIG. 10 delimits a space 124, 125 with the wall 115. For this, the walls 163 and 165 have a common periphery 168 on the major part of which they are mutually fixed in a permanent continuous manner and on a small part, for example uppermost of which they are mutually fixed via means 169 such as straps and locks, permitting opening at ill of the space 167 for housing therein of taking therefrom objects 170 which it is intended to contain and for re-closing it at will in the manner of one of the cavities 124, 125 of the bag 114 to the description of which reference should be made in this respect.

Straps such as 180 fixed to the wall 163 and placed opposite the face 164 of this permit slinging of the rucksack 162 on the shoulders of the user, as is known in itself in the field of rucksacks.

For holding against the face 166 of the wall 163 of objects 170 not occupying entirely the space 167 and to give a regular shape to the flexible wall 165, the space 167 houses a device according to the invention 171 in all respects analogous to the devices 126 and 127 previously described particularly as regards the mode of cooperation of the shell 1 with the flexible wall 165, analogous to the mode of cooperation of the shells 1 of the devices 126 and 127 with the flexible walls 119 and 120 respectively, and as regards the mode of cooperation of its wall 172 corresponding to the wall 129 of the devices 126 and 127 and delimiting as these latter with the shell 1 a fluid tight chamber 173 able to be inflated or deflated via the intermediary of a valve 174 accessible from outside the rucksack 162, with the face 166 of the wall 163 and with the possible objects 170.

Naturally, the rucksack 162 can have any desired configuration, and any appropriate arrangement to increase the ease and comfort of use. By way of non-limitative example, it can thus have on the face 164 of the wall 163, in a manner fixed to this, an elastically compressible cushion 175 for example made in the form of a fluid tight chamber 176 delimited by a fluid tight flexible wall 177 and peripherally fixed in a continuous fluid tight manner to the wall 163 also fluid tight, this chamber 176 being inflatable and deflatable via the intermediary of a valve 178, and on this cushion 175 a covering 179, for example of textile, intended to come into contact with the back of the user and facilitating a circulation of air between the back and the cushion 175.

A man skilled in the art will easily understand that the devices 126, 127, 171 which have been described can also equip other internal spaces than of a flexible bag 114 or 162, and particularly the spaces delimited by rigid walls in which the devices according to the invention have the sole function of holding objects not occupying the entirety of these spaces. One can cite by way of non-limitative examples, the baggages spaces of automotive vehicles, of boats or of aeroplanes, particularly for short and middle distance flights, stores or holds of boats, containers or the like.

In a general manner, a man skilled in the art will easily understand that the different applications of a device according to the invention which have been described and illustrated constitute only non-limitative examples, and that other applications, as well as other shapes, of devices according to the invention can be provided without departing from the scope of the present invention.

I claim:

1. A device having a rigid surrounding shell (1), delimiting an internal volume (4), and at least one internal fluid tight chamber 4, 12 to 14, 44, 61 to 63, 81, 82, 105 to 108, 130, 150, 173) occupying said internal volume (4),
   wherein the rigid surrounding shell (1) is constituted by flexible fluid tight walls (2,3) delimiting between them a fluid tight enclosure (5) held at a pressure below ambient pressure, and by a filling material (7) completely filling said fluid tight enclosure (5) held below ambient pressure, said filling material (7) having a rigid state when held below ambient pressure and having a flexible state when at ambient pressure.

2. A device according to claim 1, wherein said filling material (7) is a granular material (8) held by a support array (9) which is permeable to gases but impermeable to said granular material (8).

3. A device according to claim 1, further comprising means (6) forming a valve for access to the interior of said fluid tight enclosure (5).

4. A device according to claim 1, wherein said at least one interior fluid tight chamber entirely occupies said internal volume (7).

5. A device according to claim 1, wherein said fluid tight internal chamber is removable from said rigid shell (1).

6. A device according to claim 1, wherein said internal fluid tight chamber contains a fluid material chosen within a group consisting of gases, gels, liquids, particulate materials and an expanded material.

7. A device according to claim 6, wherein said fluid material is placed at a pressure substantially identical to ambient pressure.

8. A device according to claim 6, wherein said fluid material is placed at a pressure substantially greater than ambient pressure.

9. A device according to claim 6, further comprising means for circulating said fluid material.

10. A device according to claim 1, further comprising means (18, 35, 42, 45, 131, 156, 174) forming a valve for access to the interior of the said fluid tight chamber.

11. A device according to claim 1, further comprising a flexible cover (133, 134, 137, 138, 151, 157) enclosing said rigid shell (1) outside of said internal volume (4).

12. A device according to claim 1, wherein said rigid shell (1) entirely surrounds, in a continuous manner, said internal volume (4).

13. A device according to claim 1, wherein said rigid shell (1) has edges (25, 26, 59, 60, 75, 76, 92 to 95, 128, 154) delimiting a localized discontinuity of said rigid shell (1).

14. A device according to claim 13, wherein said edges (59, 60) are mutually adjoined and said rigid shell (1) entirely surrounds said internal volume (4).

15. A device according to claim 14, further comprising means (137) for mutual assembly of said edges (59, 60).

16. A device according to claim 15, wherein said means for mutual assembly is carried by said edges (59, 60).

17. A device according to claim 15, further comprising a flexible cover (133, 134, 137, 138, 151, 157) enclosing said rigit shell (1) outside of said internal volume (4), said means for mutual assembly (137) being carried by the said cover (137).

18. A device according to claim 13, wherein said edges (25, 26, 75, 76, 92 to 95, 128, 154) are mutually spaced and said rigid shell (1) partially surrounds, in a discontinuous manner, said internal volume (4).

19. A device according to claim 18, further comprising means (28, 41, 78, 79, 96, 97, 138, 141, 142, 155) for mutual connection of said mutually spaced edges (25, 26, 39, 75, 76, 92 to 95).

20. A device according to claim 19, wherein said means (78, 79, 96, 97, 138, 141, 142) for mutual connection are elastically deformable in extension between said edges.

21. A device according to claim 19, wherein said means (28, 41, 55) for mutual connection are elastically deformable in torsion between said edges (25, 26, 39).

22. A device according to claim 19, wherein said means (28, 41) for mutual connection are elastically deformable in compression.

23. A device according to claim 19, wherein said means (28, 41, 78, 79, 96, 97, 155) for mutual connection have at least one connection (78, 79, 96, 97) locally connecting said edges (75, 76, 92 to 95).

24. A device according to claim 19, wherein said means (28, 41, 78, 79, 96, 97, 155) for mutual connection comprises a wall (28, 41, 155) complementing said rigid shell (1) for delimiting said internal volume (4) in a continuous manner.

25. A device according to claim 19, wherein said means (28, 41, 78, 79, 96, 97, 155) for mutual connection is carried by said edges (25, 26, 39, 75, 76, 92 to 95).

26. A device according to claim 19, further comprising a flexible cover (133, 134, 137, 138, 151, 157) enclosing said rigid shell (1) outside of said internal volume (4), said means for mutual connection (138, 141, 142) being carried by said cover (138).

27. A device according to claim 19, further comprising means (86, 158) defining a determined relief inside internal volume (4).

28. A device according to claim 27, wherein said means (17, 41, 155) for mutual connection includes at least one localized projection (86, 136, 158) inside said internal volume (4).

29. A device according to claim 27, wherein said localized projection (86) is removable.

30. A device according to claim 1, further comprising means (29, 48, 133) for protection against shocks and/or frettings adhered to the said rigid shell (1) outside said internal volume (4).

31. A device according to claim 30, wherein said protection means (29, 48) is localized.

32. A device according to claim 30, wherein said protection means (29, 48) is carried by said rigid shell (1).

33. A device according to claim 30, wherein said protection means (29, 133) is carried by said cover (133, 134).

34. A device according to claim 1, further comprising at least one external fluid tight chamber (32, 52, 143, 145) adhered to said rigid shell (1) outside said internal volume (4) and containing a fluid material chosen within a group consisting of gases, gels, liquids and particulate materials.

35. A device according to claim 34, wherein said fluid material is placed at a pressure substantially identical to ambient pressure.

36. A device according to claim 34, wherein said fluid material is placed at a pressure substantially greater than ambient pressure.

37. A device according to claim 34, further comprising means (69) for circulating said fluid material.

38. A device according to claim 34, further comprising means (14) for establishing, in a predetermined manner, respective variable predetermined pressures in said external fluid tight chamber.

39. A device according to claim 34, wherein said external fluid tight chamber (32, 52) is carried by said rigid shell (1).

40. A device according to claim 34, further comprising a flexible cover (133, 134, 137, 138, 151, 157) enclosing said rigid shell (1) outside of said internal volume (4), said external chamber being carried by the said cover (138).

41. A device according to claim 1, further comprising a plurality of fluid tight chambers each of which comprises a reservoir.

42. A device according to claim 41, further comprising means for introducing a first fluid to be stored into one of said plurality of fluid tight chamber while emptying a second of said plurality of fluid tight chambers of fluid (13, 14).

43. A device according to claim 1, wherein said device comprises a floating and/or sliding device chosen within a group consisting of floats, hulls of boats, sail boards, toboggans, and skis.

44. A device according to claim 43, further comprising said rigid shell (1) has edges (25, 26, 59, 60, 75, 76, 92 to 95, 128, 154) delimiting a localized discontinuity of said rigid shell (1) and means (28, 41, 78, 79, 96, 97, 138, 141, 142, 155) for mutual connection of said edges (25, 26, 39, 75, 76, 95 to 95), said means (28, 41, 78, 79, 96, 97, 155) for mutual connection comprises a wall (28, 41, 155) complementing said rigid shell (1) for delimiting said internal volume (4) in a continuous manner, said wall (28, 41) complementing said rigid shell (1) constitutes a lower wall of the device.

45. A device according to claim 1, wherein said device is used for holding and/or supporting a human body and is chosen within a group consisting of anti-bed sore mattresses or cushions and surgical mattresses.

46. A device according to claim 45, wherein said rigid shell (1) has an upper zone (54, 72, 89) of generally flat shape, a lower zone (55, 73, 90) of generally flat shape and a peripheral zone (58, 74, 91) in the form of a skirt mutually connecting said upper and lower zones (54, 72, 89, 55, 73, 90) respectively of generally flat shape.

47. A device according to claim 46, wherein said rigid shell (1) has edges (25, 26, 59, 60, 75, 76, 92 to 95, 128, 154) delimiting a localized discontinuity of said rigid shell (1), said lower zone (51, 73, 90) is discontinuous and incorporates said edges (59, 60, 75, 76, 90 to 95).

48. A device according to claim 46, wherein a plurality of fluid tight chambers are provided with some of said plurality of fluid tight chambers forming mutually juxtaposed studs under said upper zone (54, 72, 89).

49. A device according to claim 48, wherein at least certain (62, 63, 81, 82, 105, 106) of the said plurality of fluid tight chambers have the shape of tubes of the same predetermined longitudinal direction mutually juxtaposed transversely of said direction, under said upper zone (54, 72, 89).

50. A device according to claim 49, wherein others (107, 108) of said plurality of fluid tight chambers have the shape of tubes of the same transverse direction, said tubes of the same longitudinal direction and said tubes of the same transverse direction being mutually superimposed under said upper zone (89).

51. A device according to claim 46, further comprising means (70, 85, 113) for causing in a controlled manner a succession of stages by:
 placing said fluid tight enclosure (5) at ambient pressure,
 inflating or deflating in a predetermined manner certain, predetermined ones of said plurality of fluid tight chambers,
 re-placing said fluid tight enclosure (5) at pressure below ambient.

52. A device according to claim 46, wherein said fluid tight walls are comparatively inextensible in said peripheral zone and comparatively elastically extensible in said upper zone.

53. A device according to claim 46, further comprising a flexible cover (133, 134, 137, 138, 151, 157) enclosing said rigid shell (1) outside of said internal volume (4), said cover being comparatively inextensible in a zone corresponding to said peripheral zone and comparatively elastically extensible in a zone corresponding to said upper zone.

54. A device according to claim 1, wherein said device (126, 127, 173) is adapted to hold and/or support at least one object (132, 170) in a space (124, 125, 167) having an internal contour with said surrounding rigid shell (1) taking said internal shape outside said internal volume (4).

* * * * *